(12) United States Patent
Werner et al.

(10) Patent No.: US 8,183,433 B2
(45) Date of Patent: May 22, 2012

(54) METHOD OF CONTROLLING GENE EXPRESSION IN PLANTS OR PLANT CELLS

(75) Inventors: Stefan Werner, Halle/Saale (DE); Sylvestre Marillonnet, Halle/Saale (DE); Victor Klimyuk, Halle/Saale (DE); Yuri Gleba, Halle/Saale (DE)

(73) Assignee: Icon Genetics GmbH, Munich (DE)

( * ) Notice: Subject to any disclaimer, the term of this patent is extended or adjusted under 35 U.S.C. 154(b) by 297 days.

(21) Appl. No.: 10/535,766

(22) PCT Filed: Nov. 20, 2003

(86) PCT No.: PCT/EP03/13016
§ 371 (c)(1),
(2), (4) Date: Jun. 22, 2005

(87) PCT Pub. No.: WO2004/046359
PCT Pub. Date: Jun. 3, 2004

(65) Prior Publication Data
US 2006/0037099 A1 Feb. 16, 2006

(30) Foreign Application Priority Data

Nov. 20, 2002 (DE) .................................. 102 54 167

(51) Int. Cl.
*C12N 15/82* (2006.01)
*C12N 15/00* (2006.01)
*C12N 15/09* (2006.01)
*C12N 15/33* (2006.01)

(52) U.S. Cl. ........ 800/280; 800/278; 800/279; 800/288; 435/320.1; 435/440; 435/468; 536/23.1; 536/23.72

(58) Field of Classification Search .................. None
See application file for complete search history.

(56) References Cited

U.S. PATENT DOCUMENTS

| 5,948,789 A | 9/1999 | Larsson et al. |
| 2002/0046419 A1 | 4/2002 | Choo et al. |
| 2002/0143142 A1 | 10/2002 | Lin et al. |

FOREIGN PATENT DOCUMENTS

| EP | 0 005 129 B1 | 10/1979 |
| EP | 0 166 287 B1 | 1/1986 |
| EP | 0 174 726 B1 | 3/1986 |
| EP | 0 268 956 B2 | 6/1988 |
| JP | 2000-500323 | 1/2000 |
| WO | 91/12221 A1 | 8/1991 |
| WO | 92/08716 A1 | 5/1992 |
| WO | 94/24867 A1 | 11/1994 |
| WO | 94/25028 A1 | 11/1994 |
| WO | 94/27988 A1 | 12/1994 |
| WO | WO 95/21248 | 8/1995 |
| WO | 96/02535 A1 | 2/1996 |
| WO | 96/17076 A1 | 6/1996 |
| WO | 96/17077 A1 | 6/1996 |
| WO | 97/02261 A1 | 1/1997 |
| WO | WO 98/37211 | 8/1998 |
| WO | WO 99/52563 A1 | 10/1999 |
| WO | WO0071701 | * 5/2000 |
| WO | WO 00/52146 A2 | 9/2000 |
| WO | WO 00/52146 A3 | 9/2000 |
| WO | WO 00/71701 A1 | 11/2000 |
| WO | WO0071701 | * 11/2000 |
| WO | WO 01/38488 A2 | 5/2001 |
| WO | WO 01/89283 A1 | 11/2001 |
| WO | WO0189283 | * 11/2001 |
| WO | WO 02/088369 A1 | 11/2002 |
| WO | WO02088369 | * 11/2002 |
| WO | 2004/052881 A2 | 6/2004 |

OTHER PUBLICATIONS

Mackenzie 2005 Trends in Cell Biology 15:548-554.*
Bonchio, M., et al., "The First Chiral Zirconium(IV) Catalyst for Highly Stereoselective Sulfoxidation", *J. Org. Chem.* vol. 64, No. 4, pp. 1326-1330, (1999).
Cotton, H., et al.,"Asymmetric synthesis of esomeprazole", *Tetrahedron: Asymmetry*, vol. 11, pp. 3819-3825, (2000).
Ikegami, S., et al., "Asymmetric Epoxidation of Homoallylic Alcohols Using Zirconium Tetrapropoxide, Dicyclohexyltartramide, and t-Butyl Hydroperoxide System", *Chemistry Letters*, pp. 83-84, (1987).
Nugent, W.A., "Chiral Lewis Acid Catalysis. Enantioselective Addition of Azide to Meso Epoxides", *J. Am. Chem. Soc.*, vol. 114, No. 7, pp. 2768-2769, (1992).
Jo, E., et al., "Epigenetic Regulation of Gene Structure and Function with a Cell-Permeable Cre Recombinase," *Nature Biotechnology*, 2001, pp. 929-933, vol. 19, Nature Publishing Group.
O'Donnell, P., et al., "A Novel Tomato Gene that Rapidly Responds to Wound- and Pathogen-Related Signals," *The Plant Journal*, 1998, pp. 137-142, vol. 14(1), Blackwell Science Ltd. Pearce, G., et al., "A Polypeptide from Tomato Leaves Induces Wound-Inducible Proteinase Inhibitor Proteins," *Science Reports*, 1991, pp. 895-898, vol. 23.
Will, E., et al., "Unmodified Cre Recombinase Crosses the Membrane," *Nucleic Acids Research*, 2002, pp. 1-6, vol. 30(12)e59, Oxford University Press.
Zhang, Y., et al., "Efficient and Inducible Production of Human Interleukin 6 in Chinese Hamster Ovary Cells Using a Novel Expression System," *Cytotechnology*, 1997, pp. 53-60, vol. 25, Kluwer Academic Publishers, Netherlands.
Thyagarajan, B., et al., "Mammalian genomes contain active recombinase sites," *Gene*, 2000, vol. 244, pp. 47-54.
Schmidt, E., et al., "Illegitimate Cre-dependent chromosome rearrangements in transgenic mouse spermatids," *PNAS*, 2000, vol. 97(25), pp. 13702-13707.
"Chemistry of Organisms—Chemistry in Treating Diseases from Gene Therapy to Protein Therapy," *Chemistry*, 2002, vol. 57(9), pp. 50-55.

* cited by examiner

*Primary Examiner* — Brent T Page
(74) *Attorney, Agent, or Firm* — Alston & Bird LLP

(57) ABSTRACT

A method of controlling a genetically-modified plant or plant cells, said method comprising the following steps: (a) providing a genetically-modified plant or plant cells, said plant or plant cells containing a heterologous nucleic add encoding a first polypeptide containing or consisting of a first fragment of a protein, (b) introducing a second polypeptide into cells of said genetically-modified plant or plant cells, said second polypeptide containing (i) a second fragment of said protein and (ii) a peptide sequence enabling the introduction of said second polypeptide into cells of said genetically-modified plant or plant cells, whereby said first fragment and said second fragment jointly generate a predetermined function of said protein only when jointly present.

15 Claims, 13 Drawing Sheets

Fig. 1

Protein-switch fragment

Pathogen-mediated delivery

Activation of cellular process or biochemical cascade and its spread to neighbouring cells and/or systemic spread.

SEQUENCE LISTING

<160> NUMBER OF SEQ ID NOS: 12

<210> SEQ ID NO 1
<211> LENGTH: 8573
<212> TYPE: DNA
<213> ORGANISM: Artificial Sequence
<220> FEATURE:
<223> OTHER INFORMATION: DNA sequence of the T-DNA region of vector pICH10921

<400> SEQUENCE: 1

```
tgatgggctg cctgtatcga gtggtgattt tgtgccgagc tgccggtcgg ggagctgttg      60
gctggctggt ggcaggatat attgtggtgt aaacaaattg acgcttagac aacttaataa     120
cacattgcgg acgttttaa tgtactgggg tggatgcagg tcgatctagt aacatagatg      180
acaccgcgcg cgataattta cctagtttg cgcgctatat tttgttttct atcgcgtatt      240
aaatgtataa ttgcgggact ctaatcataa aaacccatct cataaataac gtcatgcatt     300
acatgttaat tattacatgc ttaacgtaat tcaacagaaa ttatatgata atcatcgcaa     360
gaccggcaaa cgcgtttcga caaaatttag aacgaactta attatgatct caaatacatt     420
gatacatatc tcatctagat ctaggttatc attatgtaag aaagttttga cgaatatggc     480
acgacaaaat ggctagactc gatgtaattg gtatctcaac tcaacattat acttatacca     540
aacattagtt agacaaaatt taaacaacta ttttttatgt atgcaagagt cagcatatgt     600
ataattgatt cagaatcgtt ttgacgagtt cggatgtagt agtagccatt atttaatgta     660
catactaatc gtgaatagtg aatatgatga acattgtat cttattgtat aaatatccat      720
aaacacatca tgaaagacac tttctttcac ggtctgaatt aattatgata caattctaat     780
agaaaacgaa ttaaattacg ttgaattgta tgaaatctaa ttgaacaagc caaccacgac     840
gacgactaac gttgcctgga ttgactcggt ttaagttaac cactaaaaaa acggagctgt     900
catgtaacac gcggatcgag caggtcacag tcatgaagcc atcaaagcaa agaactaat     960 ccaagggctg agatgattaa ttagtttaaa aattagttaa cacgagggaa aaggctgtcg    1020
acagccaggt cacgttatct ttacctgtgg tcgaaatgat tcgtgtctgt cgattttaat    1080 tattttttg aaaggccgaa aataaagttg taagagataa acccgcctat ataaattcat     1140
atattttcct ctccgctttg aagttttagt tttattgcaa caacaacaac aaattacaat    1200
aacaacaaac aaaatacaaa caacaacaac atggcacaat ttcaacaaac aattgacatg    1260
caaactctcc aagccgctgc gggacgcaac agcttggtga atgatttggc atctcgtcgc    1320
gtttacgata atgcagtcga ggagctgaat gctcgttcca gacgtcccaa ggtaagttct    1380
gcatttggtt atgctccttg cattttaggt gttcgtcgct cttccatttc catgaatagc    1440
taagattttt tttctctgca ttcattcttc ttgcctcagt tctaactgtt tgtggtatttt   1500 ttgttttaat tattgctaca ggtccacttc tccaaggcag tgtctacgga acagacactg    1560
attgcaacaa acgcatatcc ggagttcgag atttcctta ctcatacgca atccgctgtg     1620
cactccttgg ccggaggcct tcggtcactt gagttggagt atctcatgat gcaagttccg    1680
ttcggttctc tgacgtacga catcggcggt aacttttccg cgcacctttt caaagggcgc    1740
gattacgttc actgctgcat gcctaatctg gatgtacgtg acattgctcg ccatgaagga    1800
cacaaggaag ctatttacag ttatgtgaat cgtttgaaaa ggcagcagcg tcctgtgcct    1860
gaataccaga gggcagcttt caacaactac gctgagaacc cgcacttcgt ccattgcgac    1920
aaacctttcc aacagtgtga attgacgaca gcgtatggca ctgacaccta cgctgtagct    1980
ctccatagca tttatgatat ccctgttgag gagttcggtt ctgcgctact caggaagaat    2040
gtgaaaactt gtttcgcggc cttcattttc catgagaata tgcttctaga ttgtgataca    2100
gtcacactcg atgagattgg agctactttt cagaagtccg gtgataattt aagttttttc    2160
tttcataatg agagcactct caattacacc cacagtttta gtaatataat taagtatgtg    2220
tgtaaaacgt tctttcctgc tagtcaacgg tttgtgtatc ataaggagtt tttagttact    2280
agagtcaaca cttggtactg taagtttacg agagtggata cttttactct tttccgtggt    2340
gtgtaccata ataatgtgga ttgcgaagag ttttacaagg ctatggacga tgcgtggcac    2400
```

```
tacaaaaaga cgttagcaat gcttaatgcc gagaggacca tcttcaagga taacgctgcg    2460
ttaaactttt ggttcccgaa agtgagagac atggttatcg tccctctctt tgacgcttct    2520
atcacaactg gtaggatgtc taggagagag attatggtga acaaggattt cgtttatacg    2580
gtcctaaatc acataaaaac gtatcaagct aaggctttaa cttacgcaaa tgttctgtcc    2640
tttgtggagt ctattaggtc tagagtgata attaacggtg tcactgccag gtctgaatgg    2700
gacacagaca aggcaattct aggtccatta gcaatgacat ttttccttat aacaaagttg    2760
ggtcatgtgc aggatgaaat aatcctgaaa aagttccaga agttcgacag aaccaccaat    2820
gagctgattt ggacaagtct ctgcgatgcc ctgatggggg ttattccctc ggtcaaggag    2880
acgcttgtgc gcggtggttt tgtgaaagta gcagaacaag ccttagagat aaaggttccc    2940
gagctatact gtacctttgc cgacagattg gtactacagt acaagaaggc ggaggagttc    3000
caatcgtgtg atcttttccaa acctctagaa gagtcagaga agtactacaa cgcattatcc    3060
gagctatcag tgcttgagaa tctcgactct tttgacttag aggcgtttaa gactttatgt    3120
cagcagaaga atgtggaccc ggatatggca gcaaaggtgg tcgtagcaat catgaagtca    3180
gaattgacgt tgccttttcaa gaaacctaca gaagaggaaa tctcggagtc gctaaaacca    3240 ggagagggt cgtgtgcaga gcataaggaa gtgttgagct acaaaatga tgctccgttc    3300 ccgtgtgtga aaaatctagt tgaaggttcc gtgccggcgt atggaatgtg tcctaagggt    3360
ggtggtttcg acaaattgga tgtggacatt gctgatttcc atctcaagag tgtagatgca    3420
gttaaaaagg gaactatgat gtctgcggtg tacacagggt ctatcaaagt tcaacaaatg    3480
aagaactaca tagattactt aagtgcgtcg ctggcagcta cagtctcaaa cctctgcaag    3540
gtgcttagag atgttcacgg cgttgaccca gagtcacagg agaaatctgg agtgtgggat    3600
gttaggagag gacgttggtt acttaaacct aatgcgaaaa gtcacgcgtg gggtgtggca    3660
gaagacgcca accacaagtt ggttattgtg ttactcaact gggatgacgg aaagccggtt    3720
tgtgatgaga catggttcag ggtggcggtg tcaagcgatt ccttgatata ttcggatatg    3780
ggaaaactta agacgctcac gtcttgcagt ccaaatggtg agccaccgga gcctaacgcc    3840 aaagtaatttt tggtcgatgg tgttcccggt tgtggaaaaa cgaaggagat tatcgaaaag    3900
gtaaacttct ctgaagactt gatttttagtc cctgggaagg aagcttctaa gatgatcatc    3960
cggagggcca accaagctgg tgtgataaga gcggataagg acaatgttag aacggtggat    4020
tccttcttga tgcatccttc tagaagggtg tttaagaggt tgtttatcga tgaaggacta    4080
atgctgcata caggttgtgt aaatttccta ctgctgctat ctcaatgtga cgtcgcatat    4140
gtgtatgggg acacaaagca aattccgttc atttgcagag tcgcgaactt tccgtatcca    4200
gcgcattttg caaaactcgt cgctgatgag aaggaggtta aagagttac gctcaggtgc    4260 ccggctgatg ttacgtattt ccttaacaag aagtatgacg gggcggtgat gtgtaccagc    4320
gcggtagaga gatccgtgaa ggcagaagtg gtgagaggaa agggtgcatt gaacccaata    4380
accttaccgt tggagggtaa aattttgacc ttcacacaag ctgacaagtt cgagttactg    4440
gagaagggtt acaaggatgt gaacactgtg cacgaggtgc aagggagac gtacgagaag    4500 actgctattg tgcgcttgac atcaactccg ttagagatca tatcgagtgc gtcacctcat    4560
gttttggtgg cgctgacaag acacacaacg tgttgtaaat attacaccgt tgtgttggac    4620
ccgatggtga atgtgatttc agaaatggag aagttgtcca atttccttct tgacatgtat    4680
agagttgaag cggggtcca atagcaatta cagatcgatg cagtattcag ggacagcaac    4740
ttgtttgttc agacgcccaa gtcaggagat tggcgagata tgcaatttta ctatgacgct    4800
```

```
cttcttcccg gaaacagtac tattctcaat gaatttgatg ctgttacgat gaatttgagg   4860
gatatttcct taaacgtcaa agattgcaga atcgacttct ccaaatccgt gcaacttcct   4920
aaagaacaac ctattttcct caagcctaaa ataagaactg cggcagaaat gccgagaact   4980
gcaggtttgc tggaaaattt ggttgcaatg atcaaaagaa acatgaatgc gccggatttg   5040
acagggacaa ttgacattga ggatactgca tctctggtgg ttgaaaagtt ttgggattcg   5100
tatgttgaca aggaatttag tggaacgaac gaaatgacca tgacaaggga aagtttttct   5160
agatggcttt cgaaacaaga gtcatctaca gttggtcagt tagcggactt taactttgtg   5220
gatttgccgg cagtagatga gtacaagcat atgatcaaga gtcaaccaaa gcaaaagtta   5280
gacttgagta ttcaagacga atatcctgca ttgcagacga tagtctacca ttcgaaaaag   5340
atcaatgcga ttttcggtcc aatgtttca gaacttacga ggatgttact cgaaaggatt   5400
gactcttcga gtttctgtt ctacaccaga aagacacctg cacaaataga ggacttcttt   5460
tctgacctag actcaaccca ggcgatggaa attctggaac tcgacatttc gaagtacgat   5520
aagtcacaaa acgagttcca ttgtgctgta gagtacaaga tctgggaaaa gttaggaatt   5580
gatgagtggc tagctgaggt atggaaacaa ggacacagaa aaacgacctt gaaagattat   5640
acggccggag tcaaaacatg tctttggtat caaggaaaa gtggtgatgt gacaaccttt   5700
attggtaata ccatcatcat tgcagcctgt ttgagctcaa tgatccccat ggacaaagtg   5760
ataaaggcag cttttttgtgg agacgatagc ctgatttaca ttcctaaagg tttagacttg   5820
cctgatattc aggcgggcgc gaacctcatg tggaacttcg aggccaaact cttcaggaag   5880
aagtatggtt acttctgtgg tcgttatgtt attcaccatg atagaggagc cattgtgtat   5940
tacgatccgc ttaaactaat atctaagtta ggttgtaaac atattagaga tgttgttcac   6000
ttagaagagt tacgcgagtc tttgtgtgat gtagctagta acttaaataa ttgtgcgtat   6060
ttttcacagt tagatgaggc cgttgccgag gttcataaga ccgcggtagg cggttcgttt   6120 gcttttgta gtataattaa gtatttgtca gataagagat tgtttagaga tttgttcttt   6180
gtttgataat gtcgatagtc tcgtacgaac ctaaggtgag tgatttcctc aatctttcga   6240
agaaggaaga gatcttgccg aaggctctaa cgaggttaaa aaccgtgtct attagtacta   6300
aagatattat atctgtcaag gagtcggaga ctttgtgtga tatagatttg ttaatcaatg   6360
tgccattaga taagtataga tatgtgggta tcctaggagc tgttttacc ggagagtggc   6420 tagtgccaga cttcgttaaa ggtggagtga cgataagtgt gatagataag cgtctggtga   6480
actcaaagga gtgcgtgatt ggtacgtaca gagccgcagc caagagtaag aggttccagt   6540
tcaaattggt tccaaattac tttgtgtcca ccgtggacgc aaagaggaag ccgtggcagg   6600
ttcatgttcg tatacaagac ttgaagattg aggcgggttg gcagccgtta gctctggaag   6660
tagtttcagt tgctatggtc accaataacg ttgtcatgaa gggtttgagg gaaaaggtcg   6720
tcgcaataaa tgatccggac gtcgaaggtt tcgaaggtgt ggttgacgaa ttcgtcgatt   6780
cggttgcagc atttaaagcg gttgacaact ttaaaagaag gaaaagaag gttgaagaaa   6840 agggtgtagt aagtaagtat aagtacagac cggagaagta cgccggtcct gattcgttta   6900
atttgaaaga agaaaacgtc ttacaacatt acaaacccga ataatcgata actcgagagt   6960
agtgccccaa ctgggggtaac ctttgagttc tctcagttgg gggcgtagat ccgtcgatct   7020
agtaacatag atgacaccgc gcgcgataat ttatcctagt ttgcgcgcta tattttgttt   7080
tctatcgcgt attaaatgta taattgcggg actctaatca taaaacccca tctcataaat   7140
aacgtcatgc attacatgtt aattattaca tgcttaacgt aattcaacag aaattatatg   7200
```

```
ataatcatcg caagaccggc aacaggattc aatcttaaga aactttattg ccaaatgttt    7260
gaacgatctg cttgactcta gctgggcccc tacccggggt tagggaggat tcgaacctct    7320 cactttact tattcccact gtaatacacg tcaaacgtgc gttaacaggt gatccaggaa    7380
ataaggggtt tcgatttaaa tggaacccaa aacattgcgt aatttggttt acgccacccc    7440
tacggattta caccgtaagt ctatctcttc gattcaagtg gagagaaaaa cactatgcgc    7500
tatcgtgcgc accacgctct aggggccgct ttacttgtac agctcgtcca tgccgtgagt    7560
gatcccggcg gcggtcacga actccagcag gaccatgtga tcgcgcttct cgttggggtc    7620
tttgctcagg gcggactggg tgctcaggta gtggttgtcg ggcagcagca cggggccgtc    7680
gccgatgggg gtgttctgct ggtagtggtc ggcgagctgc acgctgccgt cctcgatgtt    7740
gtggcggatc ttgaagttca ccttgatgcc gttcttctgc ttgtcggcca tgatatagac    7800
gttgtggctg ttgtagttgt actccagctt gtgccccagg atgttgccgt cctccttgaa    7860
gtcgatgccc ttcagctcga tgcggttcac cagggtgtcg ccctcgaact tcacctcggc    7920
gcgggtcttg tagttgccgt cgtccttgaa gaagatggtg cgctcctgga cgtagccttc    7980
gggcatggcg gacttgaaga gtcgtgctgc cttcatgtgg tcggggtagc ggctgaagca    8040
ctgcacgccg tagctgaagg tggtcacgag ggtgggccag ggcacgggca gcttgccggt    8100
ggtgcagatg aacttcaggg tcagcttgcc gtaggtggca tcgccctcgc cctcgccgga    8160
cacgctgaac ttgtggccgt ttacgtcgcc gtccagctcg accaggatgg gcaccacccc    8220
ggtgaacagc cctcgccct tgctcaccat ggtcaaacaa agaacaaatc tctaaccaat    8280
ctcttatctg acaaatattt aattatacta caaaaagcaa acgaagctta tcgattttt    8340 ggatgggtga ggtggagtac gcgcccgggg agcccaaggg cacgccctgg cacccgcacc    8400
gcggcttcga gcaattcatg gatccagatt gtcgtttccc gccttcagtt taaactatca    8460
gtgtttgaca ggatatattg gcgggtaaac ctaagagaaa agagcgttta ttagaataat    8520 cggatatttta aagggcgtg aaaaggttta tccgttcgtc catttgtatg tgc          8573
```

<210> SEQ ID NO 2
<211> LENGTH: 37
<212> TYPE: DNA
<213> ORGANISM: Artificial Sequence
<220> FEATURE:
<223> OTHER INFORMATION: PCR primer

<400> SEQUENCE: 2
atggaagcag tactcgacgt cgcctaaaga gaggtta                              37

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
ggcctgtggg cattcagtct g                                               21

<210> SEQ ID NO 4
<211> LENGTH: 37
<212> TYPE: DNA
<213> ORGANISM: Artificial Sequence
<220> FEATURE:
<223> OTHER INFORMATION: PCR primer

<400> SEQUENCE: 4

```
gtcgagtact gcttccatgg caaagaactg tacagcg                              37

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
tcatcgcaag accggcaaca gg                                              22

<210> SEQ ID NO 6
<211> LENGTH: 8
<212> TYPE: PRT
<213> ORGANISM: Artificial Sequence
<220> FEATURE:
<223> OTHER INFORMATION: sequence derived from Synechocystis DnaE
      extein-intein junction with AatII and NcoI sites

<400> SEQUENCE: 6

Asp Val Glu Tyr Cys Phe His Gly
1               5

<210> SEQ ID NO 7
<211> LENGTH: 38
<212> TYPE: DNA
<213> ORGANISM: Artificial Sequence
<220> FEATURE:
<223> OTHER INFORMATION: PCR primer

<400> SEQUENCE: 7
gcaagcttga cgtcaagttt gcggaatatt gcctcagt                             38

<210> SEQ ID NO 8
<211> LENGTH: 33
<212> TYPE: DNA
<213> ORGANISM: Artificial Sequence
<220> FEATURE:
<223> OTHER INFORMATION: PCR primer

<400> SEQUENCE: 8
tccctgcagt tatttaattg tcccagcgtc aag                                  33

<210> SEQ ID NO 9
<211> LENGTH: 35
<212> TYPE: DNA
<213> ORGANISM: Artificial Sequence
<220> FEATURE:
<223> OTHER INFORMATION: PCR primer

<400> SEQUENCE: 9
ggtctagaat cgatggttaa agttatcggt cgtcg                                35

<210> SEQ ID NO 10
<211> LENGTH: 37
<212> TYPE: DNA
<213> ORGANISM: Artificial Sequence
<220> FEATURE:
<223> OTHER INFORMATION: PCR primer

<400> SEQUENCE: 10
cgctgcagcc atggttaaaa caattggcgg cgatcgc                              37

<210> SEQ ID NO 11
<211> LENGTH: 74
```

-continued

```
<212> TYPE: DNA
<213> ORGANISM: Artificial Sequence
<220> FEATURE:
<223> OTHER INFORMATION: PCR primer

<400> SEQUENCE: 11
gctctcgagg ttatggcaga agttcggccc atagcccgat ccattaaaac ggctcacgac      60
gatgcgcgag cgga                                                       74

<210> SEQ ID NO 12
<211> LENGTH: 74
<212> TYPE: DNA
<213> ORGANISM: Artificial Sequence
<220> FEATURE:
<223> OTHER INFORMATION: PCR primer

<400> SEQUENCE: 12
cacggatcct catagaccgc gcgttgatcg aggtctgtcc gccgacatta attccgctcg      60
cgcatcgtcg tgag                                                       74
```

METHOD OF CONTROLLING GENE EXPRESSION IN PLANTS OR PLANT CELLS

CROSS-REFERENCE TO RELATED APPLICATIONS

This application is the U.S. National Stage of International Application PCT/EP03/13016, filed Nov. 20, 2003, which published in English on Jun. 3, 2004 and designates the U.S., and which claims the benefit of German Patent Application No. 102 54 167.1 filed Nov. 20, 2002; both of which are hereby incorporated herein in their entirety by reference.

FIELD OF THE INVENTION

The present invention relates to a method of controlling a genetically-modified plant or plant cells, notably a method of controlling a cellular process of interest in a genetically-modified plant or plant cells. The method of the invention has an exceptional biological safety. The invention further relates to a genetically-modified plant adapted for said method and to a genetically-modified plant which has been controlled according to the method of the invention. Moreover, the present invention relates to a method of producing a product in a genetically-modified plant by controlling a cellular process of interest. The method of the invention allows for the selective control of transgene expression in a transiently or stably genetically modified plant, whereby a cellular process of interest previously non-operable in the plant may be selectively switched on at any predetermined time.

BACKGROUND OF THE INVENTION

Controllable Transgene Expression Systems in Plants

One of the major problems in plant biotechnology is the achievement of reliable control over transgene expression. Tight control over gene expression in plants is essential if a downstream product of transgene expression is growth inhibitory or toxic, like for example, biodegradable plastics (Nawrath, Poirier & Somerville, 1994, *Proc. Natl. Acad. Sci.*, 91, 12760-12764; John & Keller, 1996, *Proc. Nail. Acad. Sci.*, 93, 12768-12773; U.S. Pat. No. 6,103,956; U.S. Pat. No. 5,650,555) or protein toxins (U.S. Pat. No. 6,140,075). Existing technologies for controlling gene expression in plants, are usually based on tissue-specific and inducible promoters and practically all of them suffer from a basal expression activity even when uninduced, i.e. they are "leaky". Tissue-specific promoters (U.S. Pat. No. 5,955,361; WO09828431) represent a powerful tool but their use is restricted to very specific areas of applications, e.g. for producing sterile plants (WO9839462) or expressing genes of interest in seeds (WO00068388; U.S. Pat. No. 5,608,152). Inducible promoters can be divided into two categories according to their induction conditions: those induced by abiotic factors (temperature, light, chemical substances) and those that can be induced by biotic factors, for example, pathogen or pest attack. Examples of the first category are heat-inducible (U.S. Pat. No. 5,187,287) and cold-inducible (U.S. Pat. No. 5,847, 102) promoters, a copper-inducible system (Melt et al., 1993, *Proc. Natl. Acad. Sci.*, 90, 4567-4571), steroid-inducible systems (Aoyama & Chua, 1997, *Plant J.*, 11, 605-612; McNellis et al., 1998, *Plant J.*, 14, 247-257; U.S. Pat. No. 6,063, 985), an ethanol-inducible system (Caddick et al., 1997, *Nature Biotech.*, 16, 177-180; WO09321334), and a tetracycline-inducible system (Weinmann et al., 1994, *Plant J.*, 5, 559-569). One of the latest developments in the area of chemically inducible systems for plants is a chimaeric promoter that can be switched on by the glucocorticoid dexamethasone and switched off by tetracycline (Bohner et al., 1999, *Plant J.*, 19, 87-95). For a review on chemically inducible systems see: Zuo & Chua, (2000, *Current Opin. Biotechnol.*, 11, 146-151). Other examples of inducible promoters are promoters which control the expression of pathogenesis-related (PR) genes in plants. These promoters can be induced by treatment of a plant with salicylic acid, an important component of plant signaling pathways in response to pathogen attack, or other chemical compounds (benzo-1,2,3-thiadiazole or isonicotinic acid) which are capable of triggering PR gene expression (U.S. Pat. No. 5,942,662).

There are reports of controllable transgene expression systems using viral RNA/RNA polymerase provided by viral infection (for example, see U.S. Pat. No. 6,093,554; U.S. Pat. No. 5,919,705). In these systems, a recombinant plant DNA sequence includes the nucleotide sequences from the viral genome recognized by viral RNA/RNA polymerase. The effectiveness of these systems is limited because of the low ability of viral polymerases to provide functions in trans, and their inability to control processes other than RNA amplification. Another way is to trigger a process of interest in a transgenic plant by using a genetically-modified virus which provides a heterologous nucleic acid encoding a switch for a biochemical process in a genetically-modified plant (WO02068664).

The systems described above are of significant interest as opportunities of obtaining desired patterns of transgene expression, but they do not allow tight control over the expression patterns, as the inducing agents (copper) or their analogs (brassinosteroids in case of steroid-controllable system) can be present in plant tissues at levels sufficient to cause residual expression. Additionally, the use of antibiotics and steroids as chemical inducers is not desirable or economically unfeasible for large-scale applications. When using promoters of PR genes or viral RNA/RNA polymerases as control means for transgenes, the requirements of tight control over transgene expression are also not fulfilled, as casual pathogen infection or stress can cause expression. Tissue- or organ-specific promoters are restricted to very narrow areas of application, since they confine expression to a specific organ or stage of plant development, but do not allow the transgene to be switched on at will. Recombinant viral switches as described in WO02/068664 address all these problems, but do not guarantee tight environmental safety requirements, as the heterologous nucleic acid in the viral vector can recombine.

There is abundant literature including patent applications which describe the design of virus resistant plants by the expression of viral genes or mutated forms of viral RNA (e.g. U.S. Pat. No. 5,792,926; U.S. Pat. No. 6,040,496). However, there is an environmental risk associated with the use of such plants due to the possibility of forming novel viruses by recombination between the challenging virus and transgenic viral RNA or DNA (Adair & Kearney, 2000, *Arch. Virol*, 145, 1867-1883).

Hooykaas and colleagues (2000, *Science*, 290, 979-982; WO01/89283) described the use of a translational fusion of Cre recombinase with vir gene fragments for *Agrobacterium*-mediated recombinase translocation into plant cells. Cre-mediated in planta recombination events resulted in a selectable phenotype. The translocation of Cre recombinase is the first use of a translocated protein as a switch to trigger a process of interest in plant cells. However, despite the translocation is not necessarily accompanied by DNA transfer, this approach does not guarantee high level safety, as the phytopathogenic genetically-modified microorganism (*Agrobacterium*) possesses a complete coding sequence of the switching protein Cre recombinase. Further, the process of interest can only be triggered in cells that receive the switching protein. If large ensembles of cell are to be treated, the ratio of cells receiving the switching protein to the total number of cells becomes very small. The method of Hooykaas can therefore not be applied to entire plants. Instead, its usefulness is limited to cells in tissue culture or cell culture. Further, as this method is limited to cell cultures (laboratory scale), environmental safety concerns as in large-scale or farm field applications do not arise.

It is therefore an object of the invention to provide an environmentally safe method of switching on a cellular process of interest in plants, whereby the cellular process may be selectively switched on at any predetermined time. It is another object of this invention to provide a method of switching on a cellular process of interest in entire plants. It is another object of this invention to provide a method for producing a product in a transgenic plant, wherein the production of the product may be selectively switched on after the plant has grown to a desired stage, whereby the process is environmentally safe in that genetic material necessary for said cellular process and genetic material coding for the control function are not spread in the environment together.

GENERAL DESCRIPTION OF THE INVENTION

The above objects are achieved by a method of controlling a genetically-modified plant or plant cells, said method comprising the following steps:
(a) providing a genetically-modified plant or plant cells, said plant or plant cells containing a heterologous nucleic acid encoding a first polypeptide containing or consisting of a first fragment of a protein,
(b) introducing a second polypeptide into cells of said genetically-modified plant or plant cells, said second polypeptide containing
   (i) a second fragment of said protein and
   (ii) a peptide sequence enabling the introduction of said second polypeptide into cells of said genetically-modified plant or plant cells.
whereby said first fragment and said second fragment jointly generate a predetermined function of said protein only when jointly present. Preferably, this method is performed with plants as opposed to plant cells.

The invention also provides genetically-modified plants or parts thereof obtained or obtainable by the method of the invention. Preferred parts of said plants are leaves and seeds. Seeds are most preferred examples for parts of a plant.

The invention also provides a genetically-modified plant or plant cells containing a heterologous nucleic acid encoding a first polypeptide containing or consisting of a first fragment of a protein, whereby said genetically-modified plant or plant cells and said first fragment of a protein are adapted for generating a predetermined function of said protein from said first fragment and a second fragment of said protein, whereby said second fragment can be provided to cells of said genetically-modified plant or plant cells by introducing a second polypeptide containing or consisting of said second fragment.

Further, the invention provides a system for controlling a genetically-modified plant or plant cells, comprising a genetically-modified plant or plant cells a defined above and a second polypeptide as defined above, whereby said genetically-modified plant or plant cells and said second polypeptide are designed such that said first fragment and said second fragment are jointly capable of generating a predetermined function of said protein.

The present invention provides for the first time a method of controlling a genetically-modified plant or cells thereof that is efficient in whole plants and that is, at the same time environmentally safe even when used on a large scale like in a green-house or on a farm field. The present invention allows to control a genetically-modified plant or cells thereof by introducing a second polypeptide into cells that contain a heterologous nucleic acid encoding a first polypeptide containing or consisting of a first fragment of a protein. Said second polypeptide contains a second fragment of said protein, whereby said first fragment and said second fragment jointly generate a predetermined function of said protein only when jointly present. Said predetermined function of said protein may be any function of a protein. Preferably, said function is an enzymatic activity. Said predetermined function arises only, if said first and said second polypeptide are together present in the plant, preferably in at least one cell of said plant. Said predetermined function of said protein is not generated if said second polypeptide is introduced in a plant or plant cells that do not contain said heterologous nucleic acid encoding said first polypeptide. Further, said predetermined function of said protein is not generated in plants containing said heterologous nucleic acid encoding said first polypeptide, unless said second polypeptide is introduced in cells of said plant.

In step (a) of the method of the invention, a genetically-modified plant or genetically-modified plant cells are provided. Plants are preferred. Higher plants, notably higher crop plants, are most preferred. Said plant is genetically-modified in that cells of said plant contain a heterologous nucleic acid that is involved in controlling said genetically-modified plant. Said plant provided in step (a) may be a transgenic plant, whereby most or all of the cells of said plant contain said heterologous nucleic acid stably integrated in the genome of said cells. Said heterologous nucleic acid may be stably integrated into the nuclear genome or in the genome of organelles like mitochondria or, preferably, plastids. Integration of said heterologous nucleic acid in the plastid genome is advantageous in terms of biological safety. The method of the invention is preferably carried out with transgenic plants. Alternatively, however, said plant may be transiently modified and/or said heterologous nucleic acid may be present in a fraction of cells but not in other cells. A heterologous nucleic acid in a transiently modified plant may be stably integrated in the genome of said fraction of cells or it may be present episomally. Incorporation of said heterologous nucleic acid in a fraction of cells of said plant may be achieved by transiently transfecting said organism e.g. using viral transfection or *Agrobacterium*-mediated transformation.

Said heterologous nucleic acid codes for said first polypeptide of the invention. Said first polypeptide contains or consists of a first fragment of a protein. Said first polypeptide has to be expressible from said heterologous nucleic acid. For this purpose, said heterologous nucleic acid should have a promoter for expressing said first polypeptide and other control elements necessary for expression. Said promoter may be inducible, tissue-specific, or a constitutive promoter. If it is a constitutive promoter, said predetermined function may be generated upon carrying out step (b). If the promoter is inducible, a further signal in addition to said second polypeptide may be needed for generating said predetermined function. Further, expression of said first polypeptide may be made dependent from further elements, whereby the environmental safety of the method of the invention may be increased further.

In step (b) of the method of the invention, said second polypeptide is introduced into cells of said genetically-modified plant or plant cells. Preferably, it is introduced into cells of said plant that contain said heterologous nucleic acid. If said plant is transgenic, said second polypeptide may in principal be applied to any part or to any cells of the plant. However, application to leaves is preferred. If only a fraction of the cells of said plant contains said heterologous nucleic acid, said second polypeptide is applied to the plant such that said second polypeptide can reach cells containing said heterologous nucleic acid.

Said second polypeptide contains (i) a second fragment of said protein. Further, said second polypeptide contains most preferably (ii) a peptide sequence enabling the introduction of said second polypeptide into cells of said genetically-modified plant or plant cells. The peptide sequences of items (i) and (ii) may overlap.

Said second polypeptide is most preferably introduced such that no nucleic acids encoding said second polypeptide or functional parts thereof are introduced into cells of said genetically-modified plant in step (b). A part of said second polypeptide is functional if it is capable of generating said predetermined function jointly with said first polypeptide. Said second polypeptide may be directly applied to cells of said plant. Direct application means application of said second polypeptide such that no nucleic acids encoding said second polypeptide or functional parts thereof are contained in a composition used in step (b) to apply said second polypeptide.

Directly introducing said second polypeptide may be done by (i) particle (microprojectile) bombardment, (ii) application of said polypeptide on at least a part of said plant, or (iii) by injecting a solution containing said polypeptide in tissue of said plant. In methods (ii) and (iii), said polypeptide is typically contained in a liquid, preferably aqueous, composition (or solution) that is applied to parts of the plant. Such a composition may be applied e.g. by spraying said plant with said composition containing the polypeptide. Further, said composition may be injected according to (iii).

For methods (ii) and (iii), said second polypeptide preferably comprises a membrane translocation sequence (MTS) as a peptide sequence enabling the introduction of said second polypeptide into cells of said genetically-modified plant or plant cells. Said membrane translocation sequence may be covalently or non-covalently bound to said second polypeptide. Preferably, it is covalently bound to said polypeptide. Said membrane translocation sequence may be a peptide that endows said second polypeptide with the capability of crossing the plasma membrane of cells of said plant. Many such membrane translocation sequences are known in the art. Frequently, they comprise several basic amino acids, notably arginines. The size of membrane translocation sequences may vary largely, however, they may typically have 3 to 100 amino acids, preferably 5 to 60 amino acids. Said second polypeptide may be produced by standard protein expression techniques e.g. in $E. coli$. Purification of said second polypeptide after its expression is preferably done, notably removal or destruction of nucleic acids coding for said polypeptide. Nucleic acids may be removed or destroyed by hydrolysis, preferably catalysed by an enzyme like a desoxyribonuclease (DNase) or a ribonuclease (RNase). Further or additionally, chromatographic techniques may be used for removing nucleic acids from said second polypeptide. Said second polypeptide may be applied to a plant e.g. by spraying said plant with a liquid composition, preferably an aqueous solution, containing said second polypeptide. Preferably, measures are taken to facilitate entering of said second polypeptide into cells of a plant, notably measures that allow crossing of the plant cell wall and/or the outer plant layer. An example of such measures is slight wounding of parts of the plant surface e.g. by mechanical scratching. Another example is the use of cellulose-degrading enzymes to weaken or perforate the plant cell wall.

A further technique that may be used for introducing said second polypeptide into cells in step (b) uses a pathogenic microorganism that has a secretory system capable of delivering a polypeptide into a host cell. As in said direct methods, said second polypeptide is introduced such that no nucleic acids are introduced that code for said second polypeptide or a functional part thereof. Said second polypeptide may by expressibly encoded in nucleic acids of said pathogenic microorganism, such that said second polypeptide can be expressed in said microorganism and be delivered into a cell of said plant. A preferred example of such a pathogenic microorganism is a virulent or non-virulent *Agrobacterium*, whereby said second polypeptide is not encoded in the T-DNA of a Ti-plasmid, preferably said second polypeptide is not encoded on a Ti-plasmid of the *Agrobacterium* employed. Examples of a best studied peptide sequence enabling the introduction of said second polypeptide into cells of said genetically-modified plant or plant cells using pathogenic microorganisms are vir E2 and virF proteins of *Agrobacterium* or their fragments required for protein translocation from bacterial cell into the plant cell (Vergunst et al., 2000, *Science*, 290, 979-982; WO0189283). Further, pathogenic microorganisms of the genera *Bordetella, Erwinia, Pseudomonas, Xanthomonas, Yersinia* may be used. A secretory system based on *Yersinia* is described e.g. in WO9952563.

By carrying out step (b) of the method of the invention as described above, a very high level of biological safety is achieved, since the plant does not come into contact with genetic material that could generate said predetermined function. Instead, at least one necessary component for said predetermined function is preferably provided to the plant as said second polypeptide (without genetic material coding therefore).

After performing step (b) of the method of the invention, said first fragment of said first polypeptide and said second fragment of said second polypeptide jointly generate said predetermined function of said protein when jointly present. Generation of said predetermined function may be achieved by formation of a covalent or non-covalent bonds between said polypeptides or fragments. Non-covalent bond formation may be aided by said polypeptides having a specific affinity to each other. Preferably, said first polypeptide and said second polypeptide jointly generate said predetermined function by intein-mediated trans-splicing or by intein-mediated affinity interaction. Said predetermined function may then switch on a cellular process of interest. Therefore, the protein having the generated predetermined function is also referred to herein as "protein switch". Said predetermined function of said protein switch may e.g. be a binding activity or an enzymatic activity that may act on other components for controlling said cellular process of interest. Further predetermined functions or activities of said protein switch are described below.

Said first fragment and said second fragment are generally fragments of a protein a function of which is to be (re)generated in the method of the invention. Performing the method of the invention typically requires production of nucleic acids coding for said first (notably for performing step (a)) and said second polypeptides. A sequence coding for said first polypeptide is then encoded in said heterologous nucleic acid in step (a). Said second polypeptide may be expressed separately, e.g. in bacteria like *E. coli.*

Producing nucleic acids coding for said first and second fragments may comprise splitting a nucleotide sequence coding for said protein into two or more fragments. Preferably, said nucleotide sequence coding for said protein is split into two fragments, thus obtaining a 5' and a 3' part of the nucleotide sequence. Said 5' part may correspond essentially to said first fragment. Said 3' part may correspond essentially to said second fragment. Said 5' and said 3' part may also contain regulatory sequences that may derive from a gene encoding said protein. Said nucleotide sequence is typically a coding sequence (or an open reading frame) of the protein having the predetermined function. To obtain said fragments, said nucleotide sequence is preferably split such that each obtained fragment, upon expression, is incapable of generating said predetermined function in the absence of the other fragment. Each fragment contains a sequence portion necessary for the function of the protein having the predetermined function. For example, if said protein is an enzyme, each fragment preferably contains amino acids necessary for catalysis or substrate binding of the enzyme. The protein having said predetermined function may be split into said fragments in many different ways provided that generation of said predetermined function requires all said fragments. Structural and functional information known about said protein may be helpful for finding a suitable splitting site of said nucleotide sequence. In any case, one can easily test experimentally whether a fragment generated by splitting at a randomly chosen site is capable of expressing the predetermined function encoded by said nucleotide sequence.

If the generation of the predetermined function is done by intein-mediated trans-splicing, the nucleotide sequences coding for said first and said second fragment are then joined with nucleic acids coding for intein fragments. As a result, a nucleic acid coding for said first polypeptide and a nucleic acid coding for said second polypeptide is obtained. Said polypeptides will be capable of protein trans-splicing. By said trans-splicing, said first and said second fragments are linked by peptide bond formation. Trans-splicing inteins for the use in this invention may be selected from the nucleolar and organellar genomes of different organisms including eukaryotes, archaebacteria and eubacteria. Inteins that may be used for performing this invention are listed at www.neb.com/neb/inteins.html. Also, an intein mentioned in a reference cited herein may be used. The choice of the intein might depend on the consensus sequences as well as the conditions required for efficient trans-splicing.

Said cellular process of interest may frequently require one or more additional heterologous nucleic acid in cells of said plant where said cellular process is to be controlled or switched on (cf. FIG. 8). Said predetermined function of said protein may act on said additional heterologous nucleic acid, thus switching on said cellular process of interest. Said additional heterologous nucleic acid may be present in all cells or in a fraction of cells of said plant. It may be stably incorporated in nuclear or organellar genomes of cells of said organism. What has been said regarding said heterologous nucleic acid of the invention generally applies also to said additional heterologous nucleic acid. Preferably, said plant is transgenic regarding said additional heterologous nucleic acid and regarding said heterologous nucleic acid. Said heterologous nucleic acid and said additional heterologous nucleic acid may have been introduced in said plant or into said plant cells together in step (a) of the invention, e.g. on a large heterologous construct containing them both.

With respect to said cellular process of interest, there are no particular limitations and the invention is of very broad applicability. Said cellular process of interest may be or may comprise formation of a DNA, an RNA or a protein of interest from said additional heterologous nucleic acid or involving said additional heterologous nucleic acid. There are numerous possibilities for achieving formation of said DNA, said RNA or said protein of interest. Said protein having the generated predetermined function may for example comprise a segment having a binding activity to said additional heterologous nucleic, e.g. to a promoter. Said segment may then e.g. act as a transcription factor inducing transcription of said heterologous nucleic acid, thus triggering formation of an RNA and of the protein of interest.

Preferably, said protein has a segment having an enzymatic activity capable of triggering formation of said DNA, said RNA or the protein of interest. Examples of such activities are DNA or RNA-modifying activities like the activity of a site-specific recombinase, flippase, resolvase, Integrase, polymerase, or a transposase. Said enzymatic activity may modify said additional heterologous nucleic acid leading to expression of a protein of interest e.g. by recombination. In an embodiment wherein said protein (said protein switch) has polymerase activity, said segment may be a DNA-dependent RNA polymerase that acts on a promoter of said additional heterologous nucleic acid. Said promoter is preferably not recognized by native polymerases of said plant. Examples of such promoter-polymerase systems are bacterial, viral, or bacteriophage promoter-polymerase systems like the T7 promoter-T7 polymerase. Further, said cellular process of interest may lead to formation of an expressible operon from said additional heterologous nucleic acid or from an RNA expression product of said additional heterologous nucleic acid.

Further, said DNA, said RNA or said protein of interest formed from said additional heterologous nucleic acid may be capable of spreading to other cells of said plant (e.g. a DNA or RNA viral vector). An important example of such a cellular process is the formation of an expressible amplicon from said additional heterologous nucleic acid or from an RNA expression product of said additional heterologous nucleic. Said amplicon is capable of amplifying within cells of its activation or formation (amplifying vector). Said amplicon may be an expressible amplicon that contains a gene of interest to be expressed in said cellular process of interest. Further, said amplicon may be capable of cell-to-cell or systemic movement in the plant of the invention. An amplicon may be based on a plant DNA or RNA virus. Plant RNA viruses like tobamoviruses are preferred. The amplification properties of said protein of interest capable of spreading (see below) and said amplicon may behave synergistically, thus allowing an extremely strong cellular process of interest that spreads over significant parts of said plant (e.g. leading to extremely strong expression of a protein of interest from said amplicon). Engineering of amplicons based on tobamoviruses is known in the art (see e.g. Dawson et al., 1989, *Virology*, 172, 285-293; Yusibov et al., 1999, *Curr. Top. Microbiol. Immunol.*, 240, 81-94; for review, see "Genetic Engineering With Plant Viruses", 1992, eds. Wilson and Davies, CRC Press, Inc.).

Said protein having said predetermined function may switch on formation of a DNA, an RNA or a protein of interest from said additional heterologous nucleic acid as follows. A sequence portion of said additional heterologous nucleic acid may be operably linkable to a transcription promoter by the action of said protein, which allows to switch on e.g. expression of a protein of interest or transcription of an RNA-viral amplicon from said additional heterologous nucleic acid, e.g. by operably linking a sequence encoding said protein of interest or an RNA amplicon with a promoter. There are several ways of reducing this embodiment to practice. One option is to separate, in said additional heterologous nucleic acid, the sequence encoding an RNA amplicon (or the sequence encoding a protein of interest) and a promoter by a sequence block that precludes an operable linkage therebetween. Said sequence block may be flanked by recombination sites such that said block can be cut out by a recombinase function of said protein having said predetermined function, whereby the recombinase may recognize said recombination sites. Thereby, operable linkage for transcription of the sequence encoding an RNA amplicon can be established and expression may be switched on. Another option is to have a portion of a sequence necessary for transcription (e.g. a promoter or promoter portion) in flipped orientation and flanked by recombination sites. After generation of said protein having a suitable predetermined recombinase function, said recombinase may flip said sequence portion back in correct orientation, whereby an operable linkage can be established.

In a major embodiment of the invention, said cellular process of interest involves formation of a protein of interest from said additional heterologous nucleic acid, whereby said protein of interest is capable of spreading within the plant, i.e. capable of leaving a cell of its formation and entering other cells of said plant ("spreading protein"; if the spreading protein can exert a switching function, the term "protein switch" applies also to the spreading protein). In other cells, said protein (spreading protein) may switch on a cellular process of interest, notably by controlling an additional heterologous nucleic acid. Said leaving a cell and entering other cells preferably comprises cell-to-cell-movement or systemic movement in said plant or in a part thereof. Said protein (protein switch) preferably contains a protein portion enabling said leaving a cell and entering other cells of said protein switch. Said protein portion may be a domain of a viral movement protein or of a viral coat protein. Further, said protein portion may be a plant or animal transcription factor, or a domain of a plant or animal transcription factor capable of cell-to-cell or systemic movement. Further, said protein portion may be a plant or animal peptide intercellular messenger, or a domain of a plant or an animal peptide intercellular messenger. Moreover, said protein portion may be an artificial peptide capable of enabling cell-to-cell or systemic movement. Preferably, however, said protein portion is or comprises a viral movement protein or viral coat protein, or a domain of a viral movement or coat protein.

When said protein switch capable of spreading enters other cells that contain said heterologous nucleic acid or said additional heterologous nucleic acid, it is preferably capable of switching on (inducing) expression of said protein from an (additional) heterologous nucleic acid (cf. FIG. 8). By making use of this protein (protein switch), the method of the invention allows to amplify and propagate the switching signal provided externally with said second polypeptide in said plant. Particularly, if the number of cells initially reached by said second polypeptide is small, the switching signal is efficiently carried to further cells in said plant. There are many ways how said protein switch can be made to control its own expression from said heterologous nucleic acid. These ways correspond to those that may be employed for said polypeptide of step (b) given above.

Apart from the capability of controlling its own expression, the protein switch (said protein having said predetermined function or said protein expressed from said additional heterologous nucleic acid) has preferably the capability of switching on a cellular process of interest. Although switching on of a cellular process is preferred, it is clear to those skilled in the art that the end result of a cellular process that was switched on may also be a suppression or a switching off of a process in cells of the plant. For being capable of switching on said cellular process of interest, said protein switch may have a segment that is capable of controlling said cellular process. Said segment may have a binding activity or an enzymatic activity that controls a nucleic acid (notably an additional heterologous nucleic acid) necessary for said cellular process of interest. In the method of the invention, said protein switch may achieve switching on of said cellular process analogously to the control of its own expression from an additional heterologous nucleic acid. For this purpose, said protein switch may have a segment for controlling said cellular process and a segment for causing said expression of said protein, whereby the control mechanisms of said two segments may be different. Preferably, the two control mechanisms are similar or identical, wherein one segment of said control protein may be sufficient for switching on said cellular process and for controlling the expression of said protein. Thus, for simplicity, said protein switch contains most preferably said one segment and a portion endowing said protein with the capability of leaving a cell and entering other cells of said plant.

The cellular process of interest that was switched on as described herein does, however, not have to affect the entire plant. Instead, said cellular process of interest may be limited to a part of said plant like seeds or leaves. Preferably, however, the cellular process of interest affects substantial parts of said plant. The part of a plant where said cellular process is switched on depends inter alia on the place(s) of application of said second polypeptide.

Generally, said cellular process of interest may be strongest in the vicinity of the place of application of said second polypeptide and may decrease with increasing distance from said place. Said decrease may in general be anisotropic and depend on the structure of the tissue of said plant where said second polypeptide was applied. If, for example, a cellular process of interest is to be switched on (e.g. expression of a gene of interest is to be switched on) and said second polypeptide is applied to a fraction of a leaf of the plant, said cellular process of interest typically occurs within said fraction of said leaf and in the vicinity of said fraction of said leaf. Preferably, said cellular process of interest occurs in the major part of said leaf. More preferably, said cellular process of interest occurs also in the shoot and in other leaves. Most preferably, said cellular process of interest occurs in the major part of said plant. The extent of said cellular process of interest (e.g. expression of a gene of interest) may vary within said plant e.g. with the cell type or tissue type. Obviously, application of said second polypeptide is normally not limited to a single point on the surface of a plant. Preferably, said second polypeptide is applied to several parts of said plant (see further below).

The cellular process according to the invention may comprise or give rise to a whole biochemical cascade of interest like a multi-step biosynthetic pathway in cells of the plant. The cellular process or biochemical cascade of interest is not operable in the plant prior to exposure to said second polypeptide. The method of the invention may provide control over a cellular process or biochemical cascade of interest with a hitherto unattainable technical precision and environmental safety. Thereby, novel applications in biotechnology in general, specifically in plant biotechnology, are available for solving problems which cannot be solved by conventional technologies like basal transgene expression activity in a plant, particularly when producing toxic substances or biodegradable polymers. Moreover, the precise control according to the invention allows to grow a transgenic plant to a desired stage where, for example, the plant is best suited for performing the cellular process of interest without burdening the plant with a basal expression activity slowing down the growth of the plant. Once the plant is ready for efficiently performing the cellular process of interest, the process of interest may be switched on and performed with high efficiency. Accordingly, the method of the invention allows to safely decouple the growth phase and the production phase of a multicellular organism, specifically a transgenic plant. Moreover, it is possible to design multi-component systems for multiple cellular processes or biochemical cascades of interest, whereby one or more desired processes or cascades can be selectively switched on.

DESCRIPTION OF THE FIGURES

FIG. 1 is a scheme of the method according to the invention.

(A) depicts a heterologous nucleic acid encoding PS:TP and an additional heterologous nucleic acid hNA. No external (second) polypeptide is introduced, thus the protein switch is not expressed and no cellular process of interest is switched on.

(B) an external (cell-permeable) polypeptide is introduced causing expression of the protein-switch PS:TP. The protein switch can control a cellular process by acting on hNA in the cell of its expression. Further, the protein switch can leave the cell that was triggered by said externally introduced polypeptide and enter other cells. In other cells, the protein switch can induce its own expression and also control the cellular process by acting on hNA.

Figure 5:
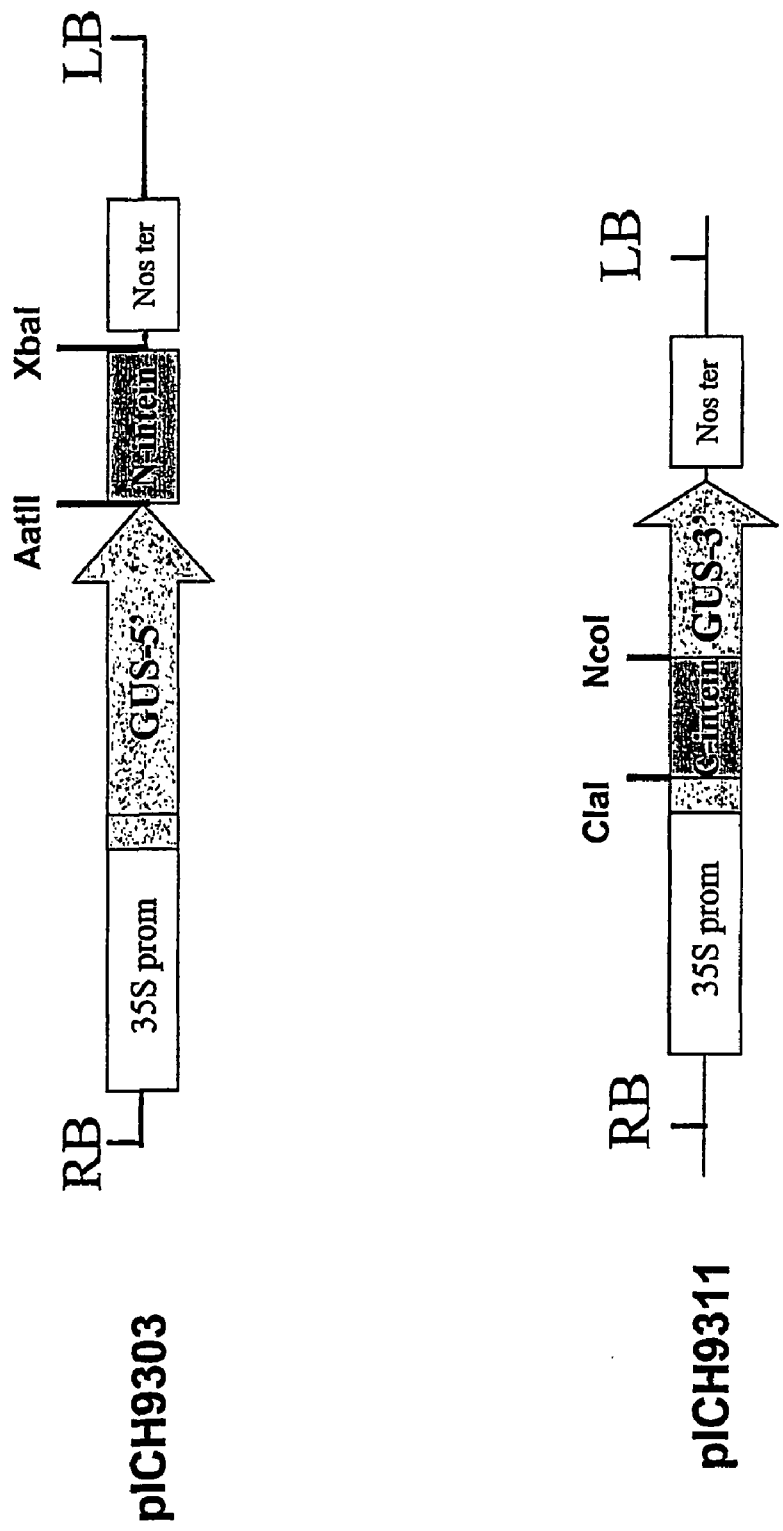

FIG. 5 depicts the constructs pICH9303 and pICH9311 designed for intein-mediated trans-splicing of the GUS protein.

Figure 6:
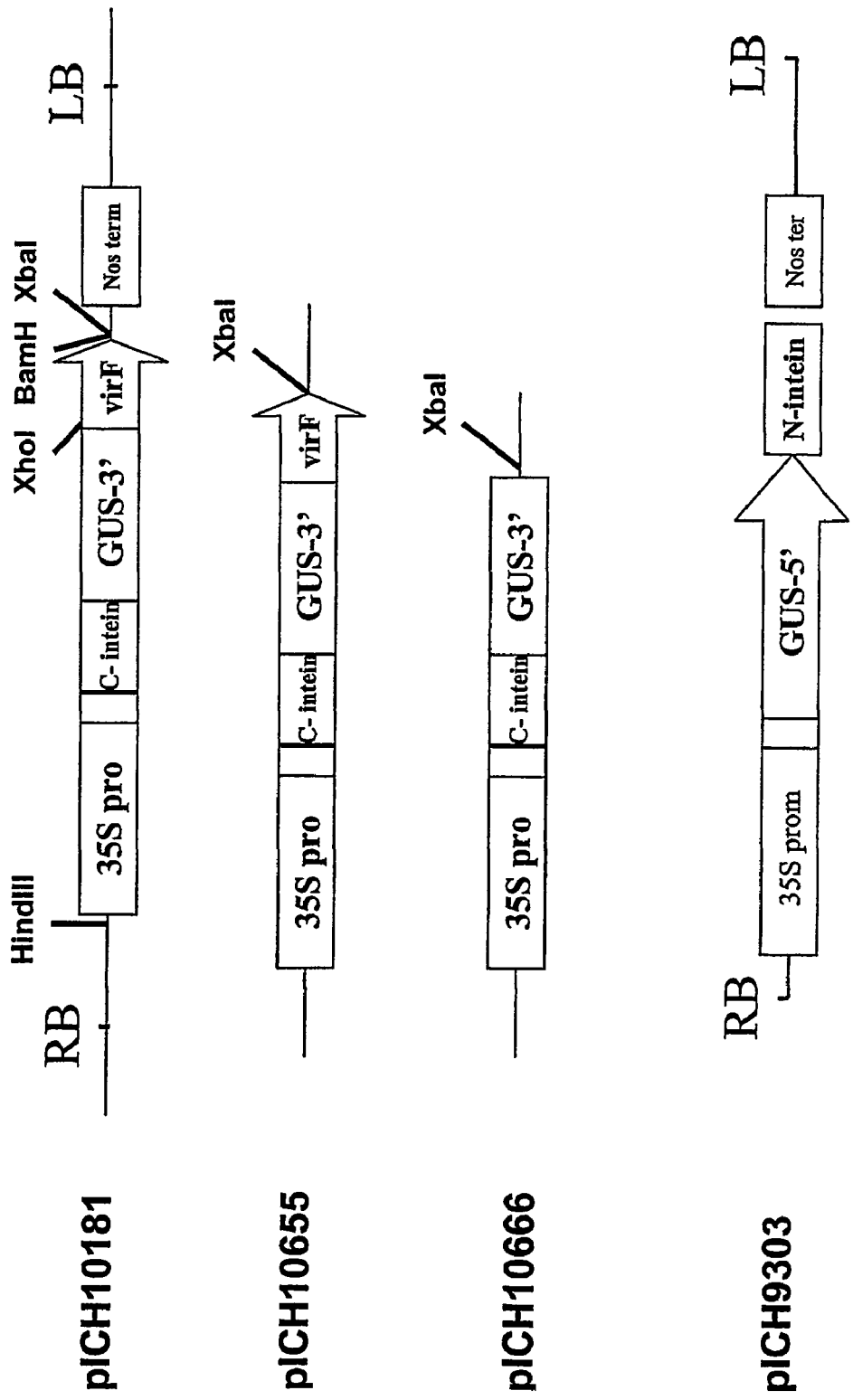

FIG. 6 depicts the constructs pICH10181, pICH1065, pICH10666 and pICH9303 designed for in planta intein-mediated trans-splicing experiments with *Agrobacterium*-mediated delivery of one of the protein components (encoded by pICH10655) necessary for trans-splicing.

Figure 7:
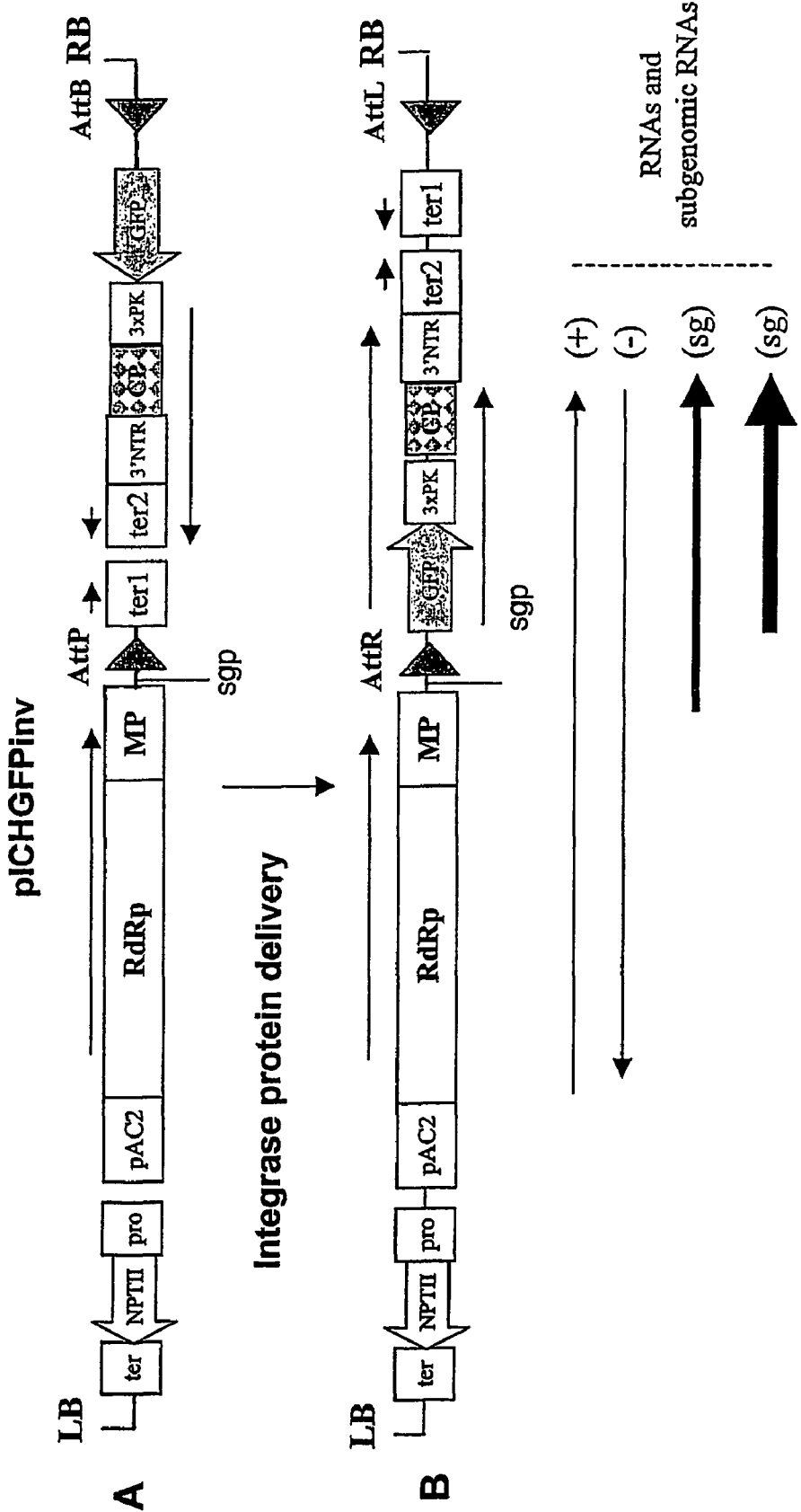

FIG. 7 depicts in (A) the construct pICHGFPinv containing a nonfunctional TMV-based provector and in (B) a functional derivative of said construct resulting from integrase-mediated recombination. Arrows at the bottom indicate RNAs and subgenomic (sg) RNAs including their orientation that can be formed from the construct shown in (B). sgp stands for subgenomic promoter.

Figure 8:
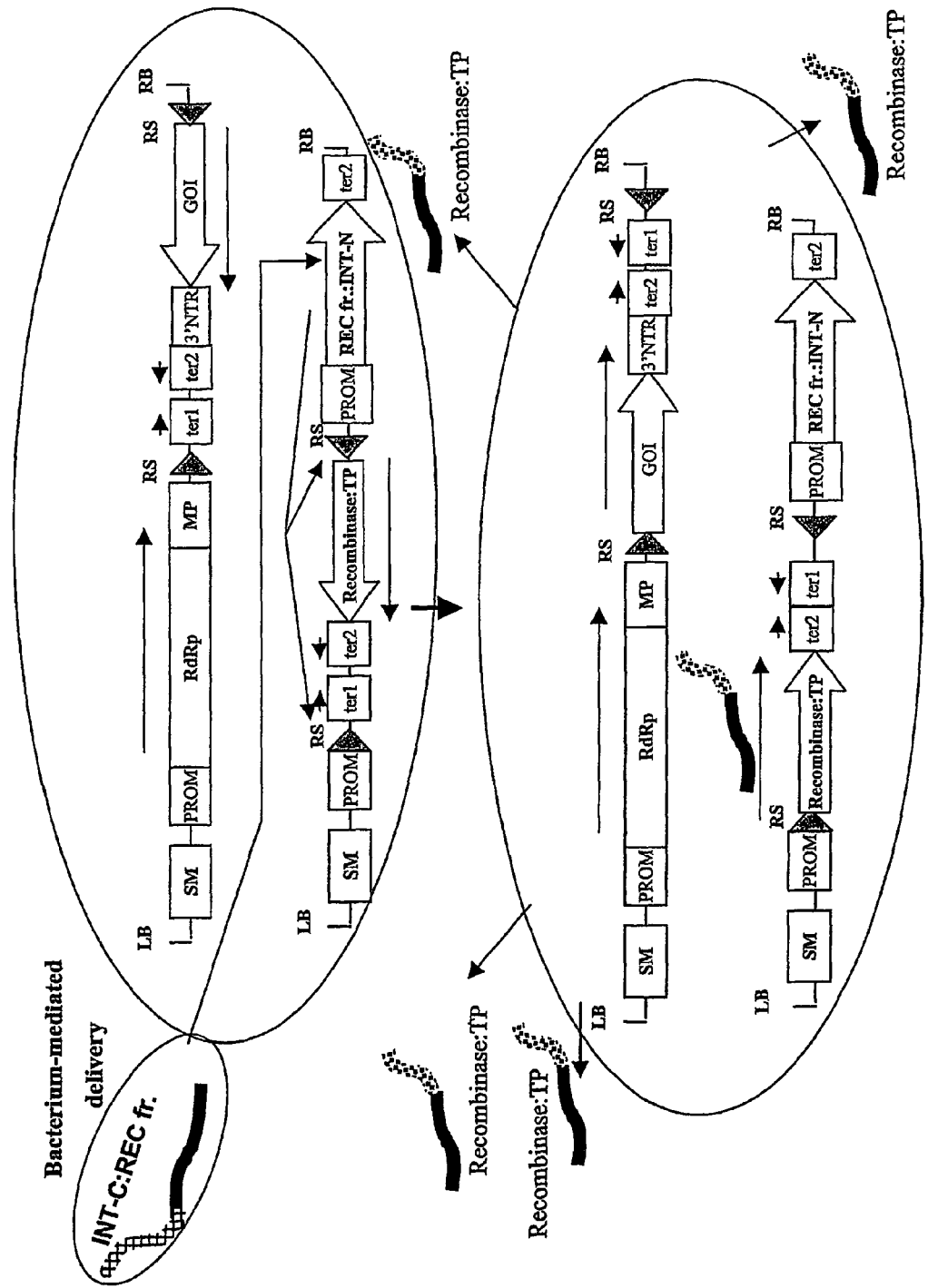

FIG. 8 depicts an embodiment wherein the bacteria-delivered protein-switch fragment (INT-C:REC fr.) triggers recombination events within targeted cells after forming an active protein switch (recombinase) by intein-mediated trans-splicing with an internally encoded fragment (REC fr.:INT-N). Said events lead to synthesis of an intracellular protein switch capable of intercellular trafficking (recombinase:TP). The intracellular protein switch can further trigger recombination events leading to rearrangement of a plant virus-based pro-vector resulting in expression of the gene of interest (GOI). MTS: membrane translocating sequence; TP: protein capable of intercellular trafficking; SM: selectable marker; RS: recombination site recognized by site-specific DNA recombinase/integrase; ter1 and ter2: transcription termination regions; PROM: promoter active in plants; RdRp: viral RNA-dependent RNA polymerase; MP: movement protein; 3'NTR: 3' non-translated region of a plant RNA virus. Arrows show the orientation of coding and regulatory sequences.

Figure 9:
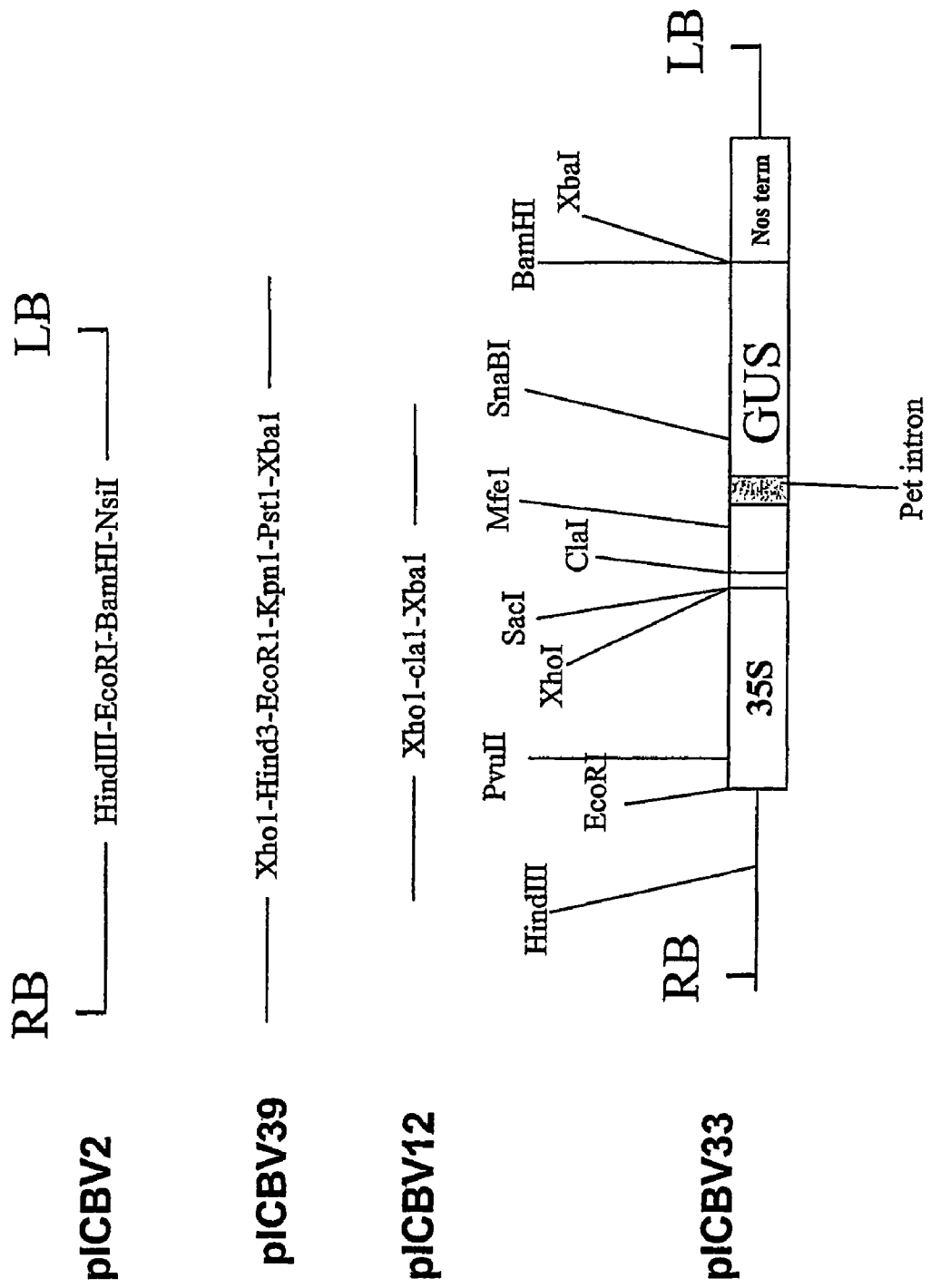

FIG. 9 depicts binary vectors pICBV2, pICBV12, pICBV33, and pICBV39.

Figure 10:
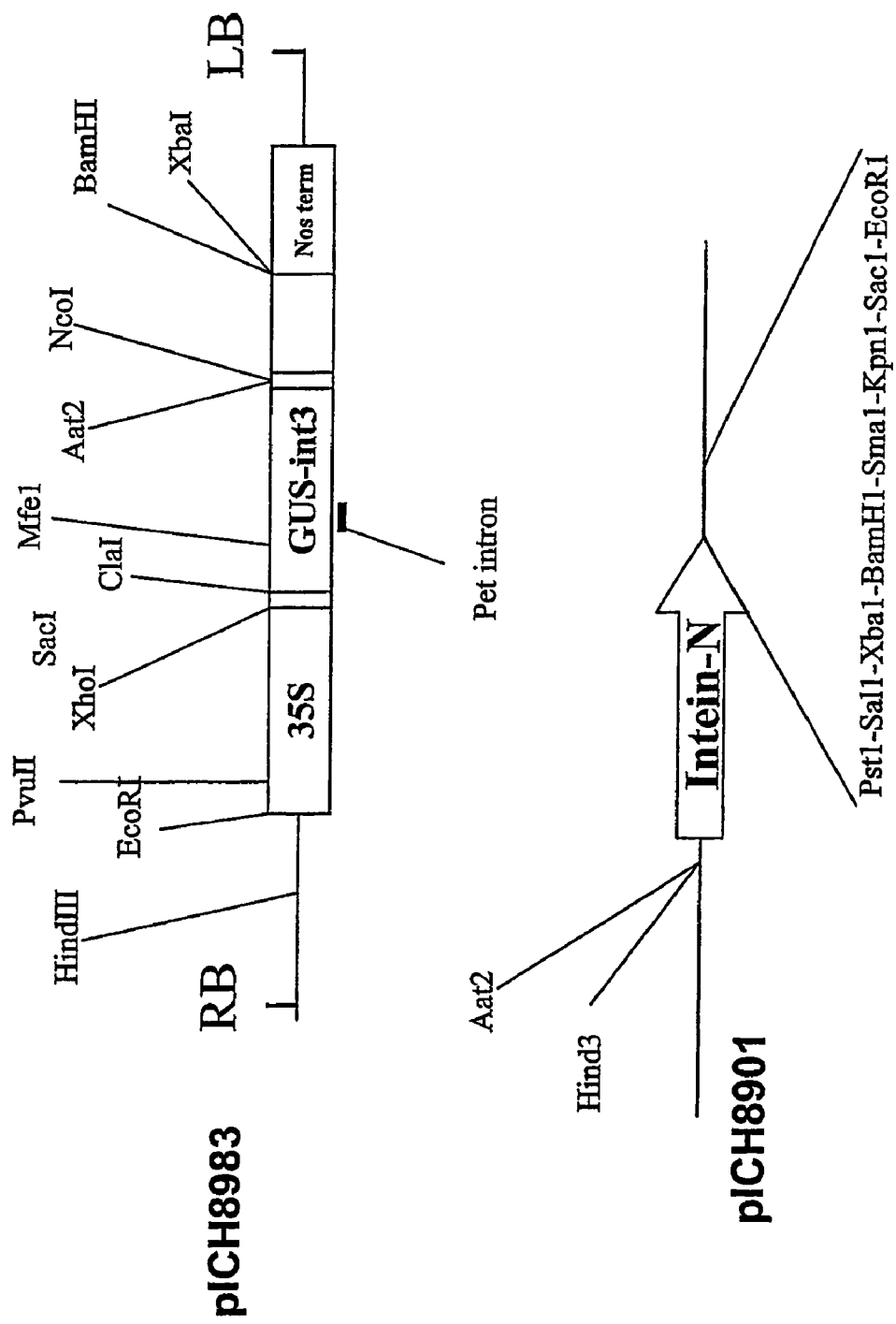

FIG. 10 depicts vectors pICH8983 and pICN8901.

Figure 11:
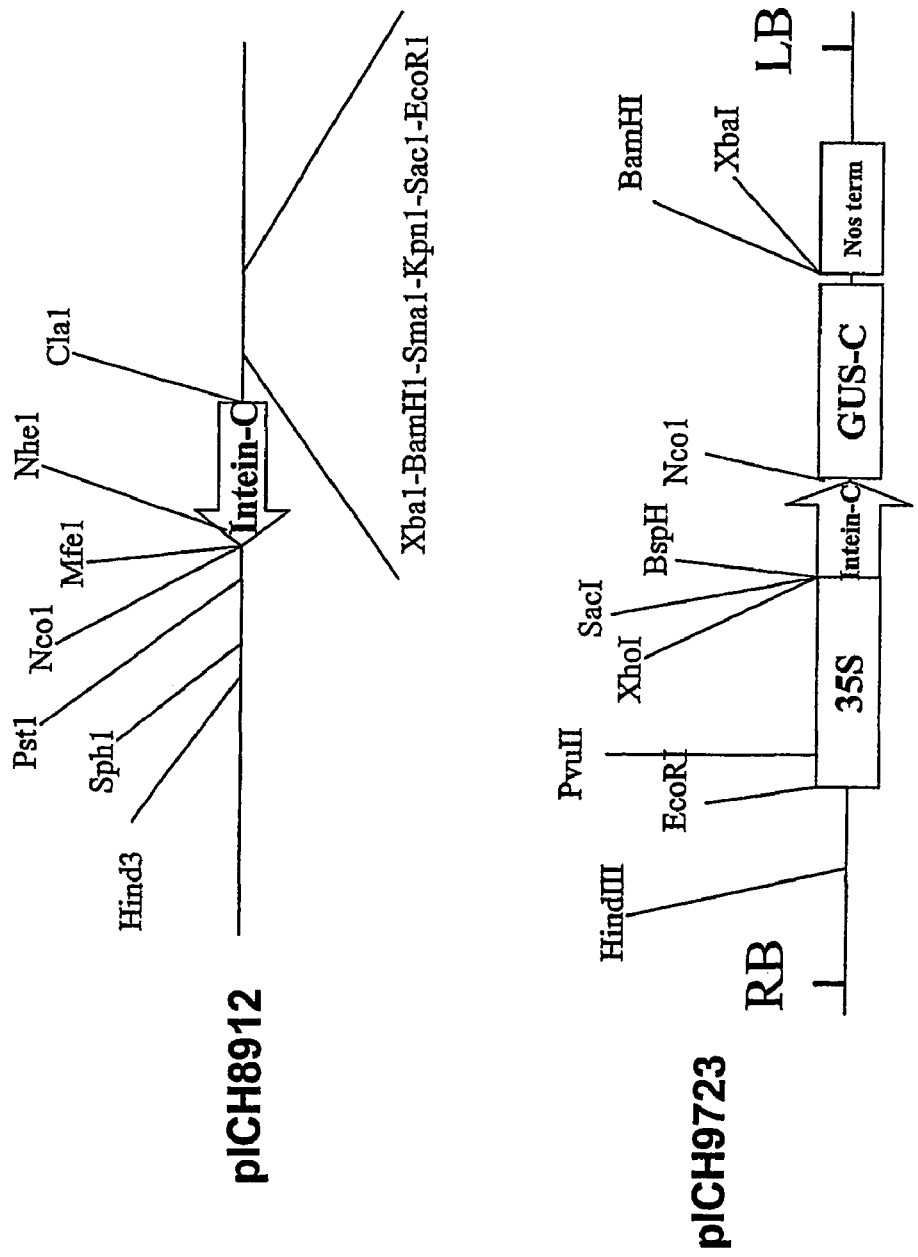

FIG. 11 depicts vectors pICH8912 and pICH9723.

Figure 12:
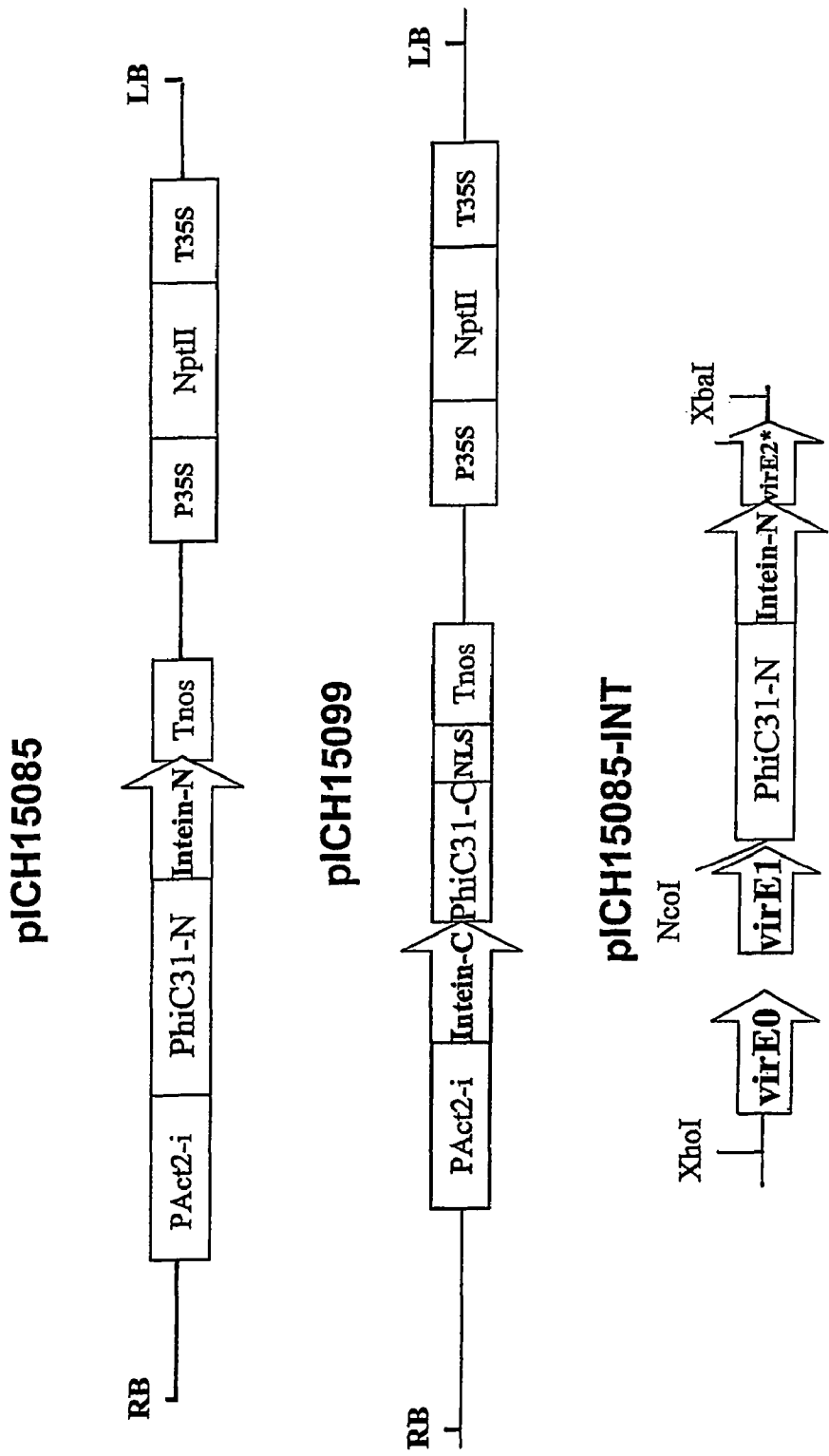

FIG. 12 depicts vectors pICH15099, pICH15085 and pICH15085-INT. Pact2-1—transcription promoter with first intron of *Arabidopsis thaliana* ACTIN2 gene; PhiC31-N—N-terminal part of integrase phiC31; PhiC31-C—C-terminal part of integrase phiC31; intein-N—N-terminal part of *Synechocystis* sp. PCC6803 DnaE intein; intein-C—C-terminal part of *Synechocystis* sp. PCC6803 DnaE Intein; NLS—nuclear localisation signal; virE—*Agrobacterial* virE operon sequences.

Figure 13:
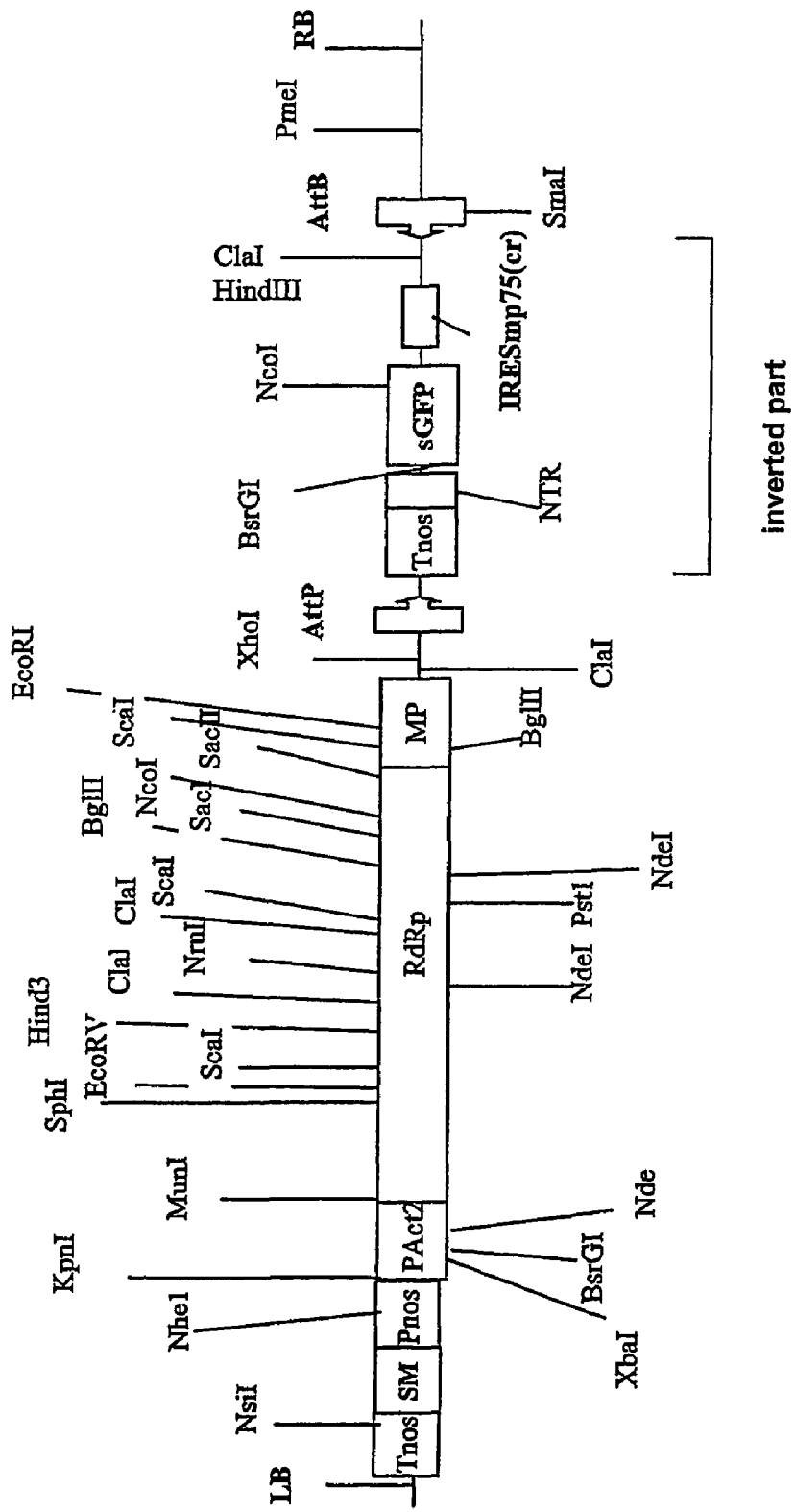

FIG. 13 depicts the T-DNA region of vector pICH10921. SM—selectable marker (NPTII gene); RdRp: viral RNA-dependent RNA polymerase; MP: movement protein; 3'NTR: 3' non-translated region of plant RNA virus; Pnos—transcription promoter of nopalin synthase; Tnos—transcription termination region of nopalin synthase; Pact2—transcription promoter of *Arabidopsis thaliana* ACTIN2 gene; IRESmp75 (cr)—IRES of movement protein of cruciferacea TMV strain; AttP and AttB—recombination sites recognised by integrase phiC31.

DETAILED DESCRIPTION OF THE INVENTION

At the basis of this invention is the use of a, preferably bacteria-mediated, delivery of protein-switch fragments into plant cells without delivery of said protein fragment-encoding nucleic acid sequence. The general principle of this invention is shown in FIG. 1.

Herein, a protein having a switching function as described above is referred to as protein switch. Thus, various proteins described herein are referred to as protein switches, e.g. said protein having said predetermined function that is jointly generated by said first and said second fragment, or said protein of interest expressed from said additional heterologous nucleic acid. The switching functions of these protein switches may be different (e.g. the enzymatic activity may be different). Preferably, the switching functions may be the same (e.g. all protein switches may have a specific recombinase activity), since a process of interest can then most efficiently be controlled. Notably, the switching functions of the protein switches may then act in common, i.e. in parallel rather than consecutively.

Choice of Protein for "Switch" Function

There are countless numbers of cellular processes of interest which can be irreversibly triggered by said predetermined function or said protein or protein switch of the invention. The protein switch can e.g. control the expression of a transgene of interest in many different ways. For example, it can trigger DNA recombination or transcription, RNA processing or translation, protein post-translational modifications etc. In addition, it, can be activated by a transgene upon delivery into the plant cell and after that be able to function as a switch. In the invention, an active protein switch may be formed by affinity interactions between an *Agrobacterium*-delivered protein switch fragment (said second fragment) and another fragment of said protein-switch encoded by the plant cell (said first fragment). Said interaction can restore protein-switch activity with (FIGS. 2A and 3A)) or without (FIGS. 2B and 3B) peptide bond formation between said fragments. Obviously, the choice of the protein switch depends on the design/choice of the cellular process to be controlled in said plant. Said cellular process can be controlled, notably switched on, by nucleic acid rearrangement or modification in cells wherein said protein switch is present or in cells that are invaded by said protein switch. In such case, the protein switch may comprise a DNA or RNA modifying enzyme like a site-specific endonuclease, a recombinase, a methylase, an integrase, a transposase, a polymerase etc.

Other possible predetermined functions of a protein switch in this invention include triggering reactions such as DNA restriction and/or DNA replication. An example of a biochemical cascade that can be triggered by restriction is a two-component system wherein a DNA sequence containing an origin of replication and being integrated into a nuclear genome is specifically excised and converted into an autosomally replicating plasmid by a rare-cutting restriction enzyme serving as protein switch, thus triggering the cascade.

There are numerous reactions (predetermined functions) that affect RNA molecules that may be used as efficient triggering device for the cellular process according to the present invention. These include, inter alia, reactions such as RNA replication, reverse transcription, editing, silencing, or translation. There is abundant prior art describing in detail how, for example, a site-specific recombinase, integrase or transposase can trigger a process of interest by DNA excision, inversion or insertion in cells, notably in plant cells (Zuo, Moller &Chua, 2001, *Nat. Biotech.*, 19, 157-161; Hoff, Schnorr & Mundy, 2001, *Plant Mol. Biol.*, 45, 41-49; U.S. Pat. No. 5,225,341; WO9911807; WO9925855; U.S. Pat. No. 5,925,808; U.S. Pat. No. 6,110,736 WO0140492; WO 0136595). Site-specific recombinases/integrases from bacteriophages and yeasts are widely used for manipulating DNA in vitro and in plants and animals. Preferred recombinases-recombination sites for the use in this invention are the following: Cre recombinase-LoxP recombination site, FLP recombinase-FRT recombination sites, R recombinase-RS recombination sites, phage C31 integrase recognising attP/attB sites etc. Transposons are widely used for the discovery of gene function in plants. Preferred transposon systems for use in the present invention include Ac/Ds, En/Spm, transposons belonging to the "mariner" family, etc.

Heterologous transcription factors and RNA polymerases may also be used in a protein switch according to the invention. For example, the delivery of T7 polymerase into cells of a plant carrying a transgene under the control of the T7 promoter may induce the expression of such a transgene.

The expression of a plant transgene of interest that is under control of a bacteriophage promoter (e.g. T3, T7, SP6, K11) with the corresponding DNA/RNA polymerase assembled in cells of a plant may be another efficient approach for the development of protein switches contemplated in this invention. Another useful approach may be the use of heterologous or chimaeric or other artificial promoters which require heterologous or engineered transcription factors for their activation. Heterologous transcription factors also can be used in order to induce expression of the transgene of interest under control of said transcription factor-recognisible promoter. Examples of such transcription factors can be, but are not limited to, yeast metalloresponsive ACE1 transcription factor binding specific sequences in the yeast MT (metallothionein) promoter (Mett et al., 1993, *Proc. Natl. Acad. Sci.*, 90, 4567-4571), different chimaeric transcription factors having a sequence-specific DNA-binding domain and an activation domain like a transcription factor having a fusion six-zink finger protein 2C7 and herpes simplex virus VP16 transcription factor activation domain (Ordiz, Barbas & Beachy, 2002, *Proc. Natl. Acad. Sci. USA*, 99, 13290-13295), transcription factor having a full length 434 repressor and the C-terminal 80 amino acids of VP16 transcriptional activator (Wilde et al., 1994, *Plant Mol. Biol.*, 24, 381-388), transcription factor used in steroid-inducible systems (Aoyama & Chua, 1997, *Plant J.*, 11, 605-612; McNellis et al., 1998, *Plant J.*, 14, 247-257; U.S. Pat. No. 6,063,985) or a tetracycline-inducible system (Weinmann et al., 1994, *Plant J.*, 5, 559-569). In some cases, the existing inducible systems for transgene expression may be used. Alternatively, heterologous transcription factors may be modified such that no activating ligand-inducer will be required to drive the transcription factor into the active state. Chimaeric transcription factors would be of advantage for the use in this invention, as they allow to combine highly sequence-specific DNA binding domains and highly efficient activation domains, thus allowing a maximum desired effect after delivery of such a factor into the plant cell.

Another protein switch contemplated under the invention may perform a posttranslational modification of one or more expression product(s) of a heterologous nucleic acid, which may lead to the activation of the expression product. There are many possible implementations of such protein switches that could operate by controlling steps such as polypeptide folding, oligomer formation, removal of targeting signals, conversion of a pro-enzyme into an enzyme, blocking enzymatic activity, etc. For example, delivery of a site-specific protease into cells of a plant may trigger a cellular process of interest if a genetically-engineered host specifically cleaves a pro-enzyme, thus converting it into an active enzyme, if a product is targeted to a particular cellular compartment because of the host's ability to cleave or modify a targeting motif, or if a product is specifically mobilised due to the removal of a specific binding sequence. Cleavage of a translational fusion protein can be achieved via a peptide sequence recognized by a viral site-specific protease or via a catalytic peptide (Dolja et al., 1992, *Proc. Natl. Acad. Sci. USA*, 89, 10208-10212; Gopinath et al., 2000, *Virology*, 267, 159-173; U.S. Pat. No. 5,162,601; U.S. Pat. No. 5,766,885; U.S. Pat. No. 5,491,076). Other examples of site-specific proteases applicable to this invention are mammalian enterokinases, for example, human enterokinase light chain which recognizes the sequence DDDK-I (Kitamoto et al., 1994, *Proc. Natl. Acad. Sci.*, 91, 7588-7592), and specifically cleaves Lys-Ile bonds; viral proteases, like Hc-Pro (Carrington J C & Herndon K L, 1992, *Virology*, 187, 308-315) which catalyses proteolysis between the Gly-Gly dipeptide but requires 4 amino acids for the recognition of the cleavage site; site-specific protease of Semliki Forest Virus (Vasiljeva et al., 2001, *J Biol. Chem.*, 276, 30786-30793); and proteases involved in polyubiquitin processing, ubiquitin-carboxy-terminal hydrolases (Osava et al., 2001, *Biochem Biophys Res Commun.*, 283, 627-633).

Pathogene-Mediated Delivery of Said Second Polypeptide (Protein Switch Fragment) into the Plant Cell Plant pathogens have very efficient systems for delivering effector proteins into plant cells. Many plant and animal pathogenic bacteria use a specialized secretion systems to deliver effector proteins directly into the host cells. There are many descriptions in the literature of such secretory systems, for example the type III secretion system for gram-negative bacteria (Binet et al., 1997, *Gene*, 192, 7-11; Thanassi & Hultgren, 2000, *Curr. Opin. Cell Biol.*, 12, 420-430; Buttner & Bonas, 2002, *Trends Microbiol.*, 10, 186-192; Buttner & Bonas, 2003, *Curr. Opin. Plant Biol.*, 6, 312-319), type II secretory system for proteobacteria (Sandkwist, 2001, *Mol. Microbiol.*, 4, 271-283). Multiple pathways of protein secretion from bacteria are described in the review of Thanassi and Hultgren (2000, *Curr. Opin. Cell Biol.*, 12, 420-430). Type III secretion systems of different phytopathogenic bacteria can be used for the delivery of a heterologous protein of interest into plant cells. For example, the Hrp gene cluster (type III protein secretion) was cloned from *Erwinia chrysanthemi* (Ham et al., 1998, *Proc. Natl. Acad. Sci. USA*, 95, 10206-10211); *Pseudomonas syringae* secretion system is described with sufficient for using in this invention details (for review see Jin et al., 2003, *Microbes Infect.*, 5, 301-310); secretory system of *Xanthomonas campestris* is being intensively studied (Marois et al., 2002, *Mol. Plant. Microbe Interact.*, 15, 637-646; Szurek et al., 2002, *Mol. Microbiol.*, 46, 13-23).

Preferably, phytopathogens causing little damage to the host plants are used for the present invention. More preferably, phytopathogens are engineered such that they are able to transfer a heterologous protein of interest without causing any ill effect on the host plant. Some non-pathogenic bacteria can be engineered such that they possess only that part of the type III secretion system that is necessary for the delivery of the heterologous protein of interest into the plant cell. Some gram-negative bacteria, like *Agrobacterium tumefaciens* and *Agrobacterium rhizogenes*, are well studied and are widely used for introducing recombinant DNA into the plant cells (Zambryski, 1988, *Annu Rev Genet.*, 22, 1-30; Hiei, Komari & Kubo, 1997, *Plant Mol. Biol.*, 35, 205-18; Newell, 2000, *Mol. Biotechnol.*, 16, 53-65). They are able to deliver T-DNA into the nuclei of many plant species and the mechanism of such transport is reasonably well studied (Hooykaas & Beijersbergen, 1994, *Annu. Rev. Phytopathol.*, 32, 157; Zupan & Zambryski, 1995, *Plant Physiol.*, 107, 1041-1047; Hansen & Chilton, 1996, *Proc Natl Acad Sci USA*, 93, 14978-1483). *Agrobacteria* are possibly the most suited for the use in this invention. The publication of Hooykaas group (2000, *Science*, 290, 979-982) demonstrates the possibility of *Agrobacterium*-mediated transfer into the host cell of heterologous protein Cre recombinase. The transfer was achieved by using the translational fusion of Cre with Virulence proteins or their parts involved in protein translocation into the plant cell during the contact with *Agrobacterium*. The Cre recombinase delivery was not coupled with transfer of DNA encoding said recombinase, but was efficient enough to trigger recombination events in engineered target cells. The process of bacterium-mediated delivery of a polypeptide (said second polypeptide) into the plant cell requires the availability of engineered bacterial cells carrying the gene of said protein (WO0189283). Such process is efficient enough to trigger selectable changes in affected plant cells, but has some serious disadvantages that significantly restrict the applicability of said invention. Firstly, it does not provide control over transgene segregation, as the entire coding sequence for said polypeptide is present in the phytopathogenic bacteria. Secondly, it is not efficient enough to have practical applications, as the changes triggered by the protein-switch are restricted to the cells which were the primary receptors of said polypeptide.

Control Over Transgene Segregation Encoding the Protein-Switch

Therefore, either a very efficient method of delivering said second polypeptide to each or most of the cells of the targeted plant or an efficient spread of events triggered by the protein switch or the combination of both approaches is required. Also, to make the protein switch system safe, strict control over the heterologous nucleic acid encoding said protein switch is desired. This can be achieved either by using direct polypeptide application (e.g. treating plants with the solution containing said second polypeptide), or by using bacterial delivery of said second polypeptide, whereby only a part of said protein switch is supplied by bacteria, but another part (said first polypeptide) is encoded by the targeted plant cell.

In order to address these issues it is proposed herein to use a "split genes" (or "split proteins") approach for controlling the segregation of a transgene encoding said protein switch, notably of the protein having said predetermined function. In this embodiment, an active (functional) protein-switch is assembled either by intein-mediated protein trans-splicing (FIG. 2-A and FIG. 3-A) or by affinity interaction (FIG. 2-B and FIG. 3-B) from said first and said second fragment of said first and said second polypeptide, respectively. This is an especially important issue for phytopathogen-mediated delivery of a protein with a switching function.

In Example 1 of this invention we demonstrate the efficiency of in planta intein-mediated GUS trans-splicing in plant cells using the constructs shown in FIG. 5. Trans-splicing restores very efficiently the GUS activity, which is comparable with that from control experiments. In Example 2 of this invention we demonstrate the efficiency of this approach by delivering one part of the GUS protein into the plant cell as a translational fusion with the C-terminal end of the virF protein (FIG. 6). Delivery of such fusions with the help of an agrobacterial secretory system leads to the formation of a functional GUS protein by intein-mediated trans-splicing, if another fragment of the GUS protein is either encoded within plant cell by stably integrated T-DNA or even co-delivered with another strain of *Agrobacterium*. In both cases, the protein switch does not exists as a continuous DNA sequence and its use is much better controlled and biologically safe.

Figure 2:
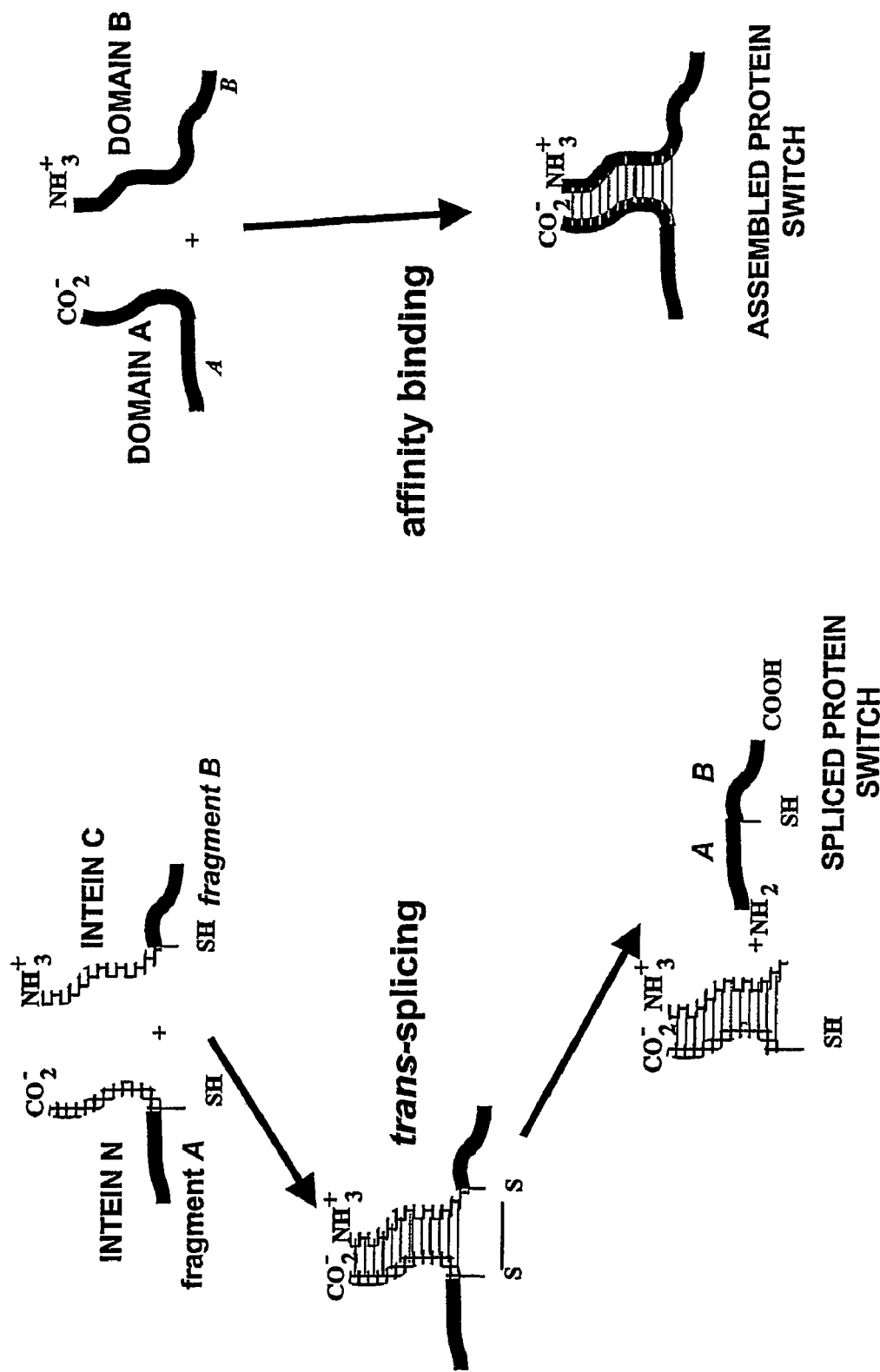
FIG. 2 is a scheme showing embodiments for generating an active protein switch from inactive protein fragments in a plant cell. A: generation of an active protein switch by intein-mediated trans-splicing of protein fragments. B: generation of an active protein switch by affinity binding of protein fragments.

Intein-mediated trans-splicing of proteins with restoration of their activity is known in the prior art and is described in detail in many publications. Protein affinity interaction and/or trans-splicing can be achieved by using engineered inteins (FIG. 2-A). Inteins were first identified as protein sequences embedded in-frame within protein precursor and excised during protein maturation process (Perler et al., 1994, *Nucleic Acids Res.*, 22, 1125-1127; Perler, F. B., 1998, *Cell*, 92, 1-4). All information and catalytic groups necessary to perform a self-splicing reaction reside in the intein and two flanking amino acids. The chemical mechanism of protein splicing is described in detail by Perler and colleagues (1997, *Curr. Opin. Chem. Biol.*, 1, 292-299) and by Shao & Kent (1997, *Chem. Biol.*, 4, 187-194). Inteins usually have N- and C-terminal splicing regions and a central homing endonuclease region or small linker region. Over 100 inteins are known so far that are distributed among the nuclear and organellar genomes of different organisms including eukaryotes, archaebacteria and eubacteria (www.neb.com/neb/inteins.html). It was shown that inteins are capable of trans-splicing. The removal of the central homing endonuclease region does not have any effect on intein self-splicing. This made possible the design of trans-splicing systems, in which the N-terminal and C-terminal fragments of an intein are co-expressed as separate fragments and, when fused to exteins (protein fragments that are ligated together with the help of the intein), can perform trans-splicing in vivo (Shingledecker et al., 1998, *Gene*, 207, 187-195). It was also demonstrated with N- and C-terminal segments of the *Mycobacterium tuberculosis* RecA intein, that protein trans-splicing can take place in vitro (Mills et al., 1998, *Proc. Natl. Acad. Sci. USA*, 95, 3543-3548). This phenomenon was also identified for the DnaE protein of *Synechocystis* sp. strain PCC6803 (Wu et al., 1998, *Proc. Natl. Acad. Sci. USA*, 95, 9226-9231). Two different genes located more than 700 Kb.p. apart on opposite DNA strands encode this protein. It was also shown that two intein sequences encoded by those genes reconstitute a split mini-intein and are able to mediate protein trans-splicing activity when tested in *Esherichia coli* cells. An intein of the same origin (DnaE intein from *Synechocystis* sp. strain PCC6803) was used to produce functional herbicide-resistant acetolactate synthase II from two unlinked fragments (Sun et al., 2001, *Appl. Environ. Microbiol.*, 67, 1025-29) and 5-enolpyruvylshikimate-3-phosphate synthase (EPSPS) (Chen et al., 2001, *Gene*, 263, 39-48) in *E. coli*.

Figure 3:
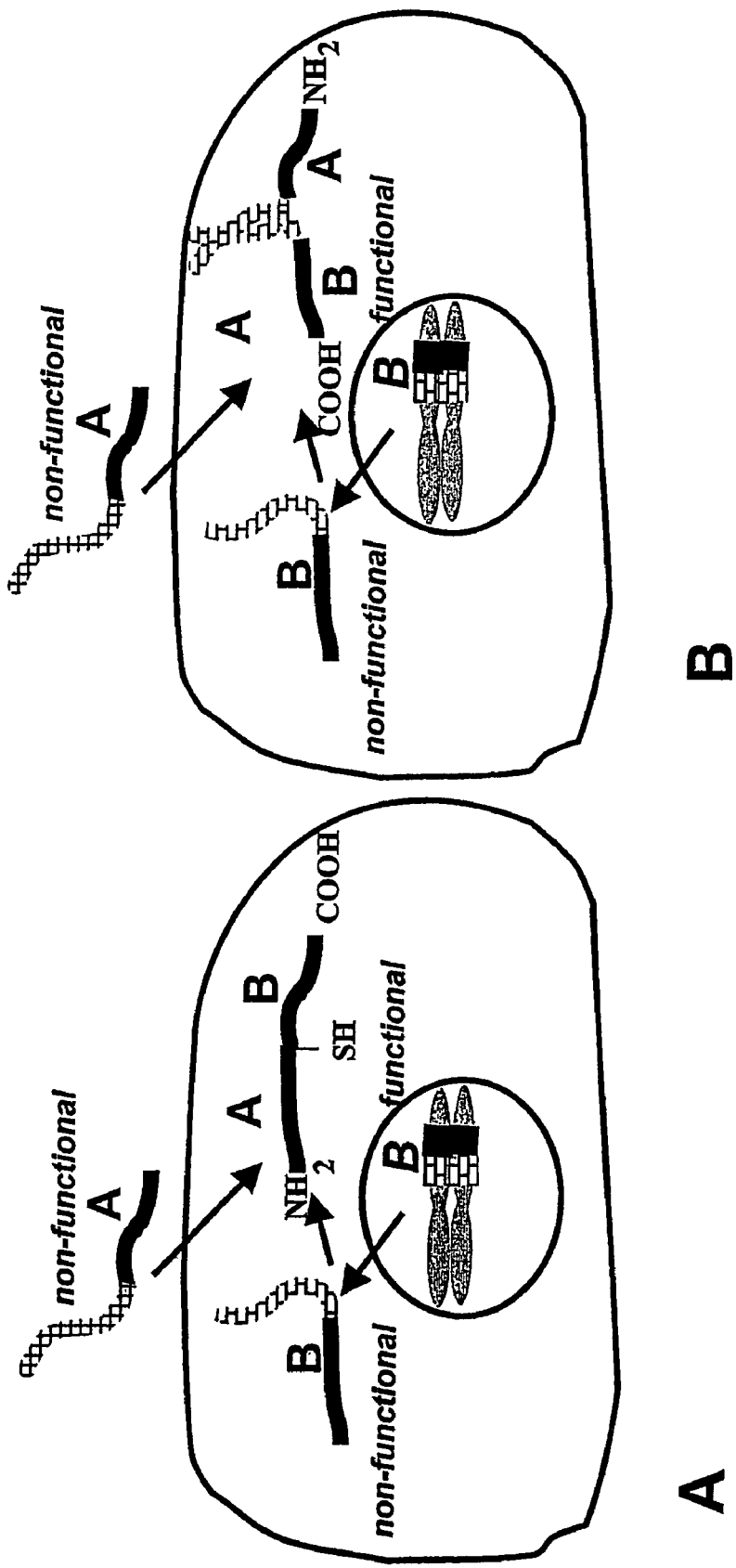
FIG. 3 is a scheme showing assembly of a functional protein (AB) from non-functional protein fragments A and B by intein-mediated trans-splicing (FIG. 3A) or affinity interaction (FIG. 3B). Fragment A is the second polypeptide of the invention that is introduced into the cell. Fragment B is internally expressed from a heterologous nucleic acid.
Figure 4:
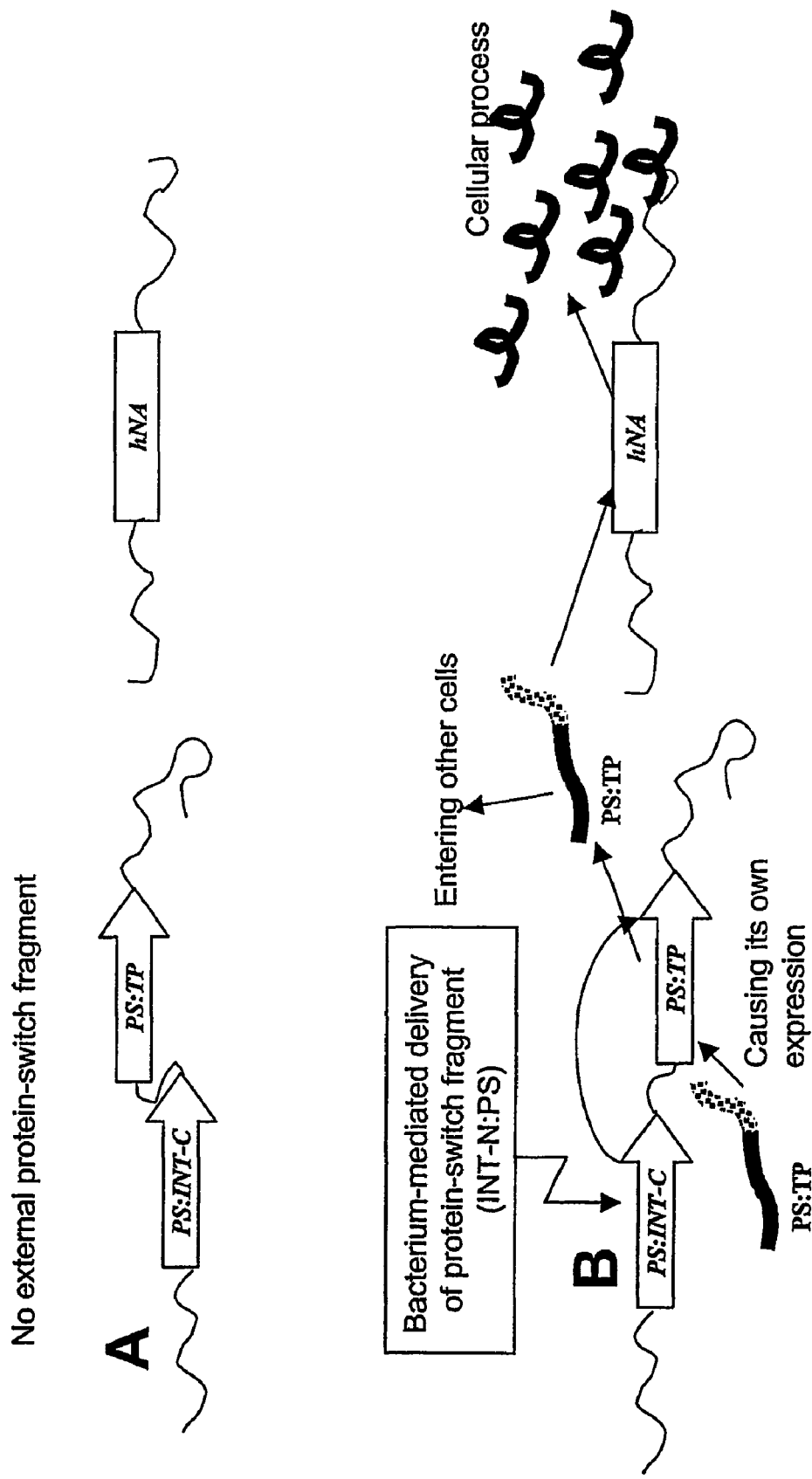
FIG. 4 is a general scheme showing switching on a cellular process of interest via a protein-switch that is capable of intercellular trafficking and causing its own expression in other cells. PS stands for protein switch, TP stands for a trafficking protein capable of intercellular trafficking (i.e. leaving a cell and entering other cells), PS:TP stands for a PS-TP fusion protein, hNA stands for an additional heterologous nucleic acid.

Trans-splicing of protein fragments (including covalent bond formation between exteins) is not necessarily required to restore the original function of the split protein. In many cases, affinity interaction between protein fragments without peptide bond formation is sufficient to restore protein function (FIG. 2-B). This approach is most successful (as in case of intein-mediated trans-splicing) with proteins having two or more functional domains. In this case, the domains can be separated from each other by splitting the coding sequence between two transcription vectors and brought together through protein-mediated affinity interactions (FIG. 3-B). Protein domains can interact without the necessity to use interacting inteins. There is an example of reconstituting activity of IS10 transposase consisting of two structural domains connected by a proteolysis-sensitive linker region (Kwon, Chalmers & Kleckner, 1995, *Proc. Natl. Acad. Sci. USA*, 92, 8234-8238). Each of the domains separately is unable to provide for transposase function. When added together, however, they are able to provide for transpositions even without being connected by a linker region. There are many other examples of functional protein reconstitution from isolated fragments without peptide bond formation. The efficient assembly of a functional insulin receptor binding site was achieved by simple mixing of non-functional fragments (Kristensen et al., 2002, *J. Biol. Chem.*, 277, 18340-18345). The reconstitution of active proteins by simple mixing of two inactive peptide fragments was shown for leucine dehydrogenase (Oikawa et al., 2001, *Biochem. Biophys. Res. Commun.*, 280, 1177-1182), $Ca^{2+}$-binding protein calbindin D28k (Berggard et al., 2000, *Protein Sci.*, 9, 2094-2108; Berggard et al., 2001, *Biochemistry*, 40, 1257-1264), *Arabidopsis* developmental regulator COP1 (Stacey et al., 2000, *Plant Physiol.*, 124, 979-990), diopamine D receptor (Scarselli et al., 2000, *Eur. J. Pharmacol.*, 397, 291-296), microplasminogen (De Los Santos, Wang & Reich, 1997, *Ciba Found. Symp.*, 212, 76-83) and many others.

Leucine zipper domains are of special interest for forming protein heterodimers once fused to protein fragments of interest (Riecker & Hu, 2000, *Methods Enzymol.*, 328, 282-296; Liu et al., 2001, *Curr. Protein Pept. Sci.*, 2, 107-121). An interesting example is the control of protein-protein interaction with a small molecule. For example, Cre recombinase was engineered in such a way that, when split in two inactive fragments, was able to restore 100% of its recombinase activity at the presence of small molecule rapamycin that triggered activity complementation through heterodimerization between two inactive fragments (Jullien et al., 2003, *Nucleic Acids Res.*, 31, e131). Rapamycin and its non-toxic analogs also can be used for conditional protein splicing, whereby they trigger a trans-splicing reaction (Mootz et al., 2003, *J. Am. Chem. Soc.*, 125, 10561-10569). Similar approaches for regulation of protein-protein interactions with the help of small molecules, such as rapamycin or rapamycin analogs, are described in several papers (Amara et al., 1997, *Proc. Natl. Acad. Sci. USA*, 94, 10618-10623; Pollock et al., 2000, *Proc. Natl. Acad. Sci. USA*, 97, 13221-13226; Pollock et al., 2002, *Nat. Biotechnol.*, 20, 729-733). Many other chemical dimerizers such as dexamethasone and methotrexate can be used for assembling active homo- or heterodimers from inactive protein fragments (for review see: Pollock & Clackson, 2002, *Curr. Opin. Biotechnol.*, 13, 459-467).

Affinity interactions can be efficiently engineered by using naturally occurring interacting protein domains or by identifying such domains with the help of two-hybrid (Fields & Son, 1989, *Nature*, 340, 245-246; Chien et al., 1991, *Proc. Natl. Acad. Sci. USA*, 88, 9578-9582; *Yeast Protocol Handbook*, Clontech Laboratories, Inc., 2000) or phage display systems. For example, phage display may be used to select a 5-12-mer oligopeptide with high affinity to a protein fragment of interest. Several such systems are now commercially available. Phage display is a selection technique in which a short variable 5-12-mer oligopeptide is inserted into a coat protein of bacteriophage. The sequence encoding this variable oligopeptide is included in the corresponding gene of the bacteriophage coat protein. Usually, a 7-mer phage display library has at least $10^9$ independent clones bearing different combinations of 7-mer amino acids in variable oligopeptides. Phage display has been used to create affinity complexes between bacteriophage and a protein of interest, allowing rapid identification of peptide ligands for a given target protein by an in vitro selection process called "panning" (Parmley, Smith, 1988, *Gene* 73, 305-318; Cortese et al., 1995, *Curr. Opin. Biotechnol.*, 6, 73-80). The phage-protein complex created after the panning procedure can be dissociated and a phage with affinity to a target protein can be amplified. Usually, one needs three panning cycles to get bacteriophage with high affinity. After three rounds, individual clones can be characterized by sequencing of variable region in genomic DNA. Said system can be efficiently adopted for identifying short interacting oligopeptides and using them as affinity tags in order to bring together protein fragments.

Another approach includes the use of naturally occurring interacting domains like leucine-rich repeats (Kobe & Deisenhofer, 1994, *Trends Biochem Sci.*, 19, 415-421; Kobe & Kajava, 2001, *Curr. Opin. Struct. Biol.*, 11, 725-732), zinc finger (Grossley, Merika & Orkin, 1995, *Mol. Cell. Biol.*, 15, 2448-2456), ankyrin repeats (Thompson, Brown & McKnight, 1991, *Science*, 253, 762-768), chromo domains (Paro & Hogness, 1991, *Proc. Natl. Acad. Sci. USA*, 88, 263-267; Singh et al., 1991, *Nucleic Acids Res.*, 19, 789-793) and many others involved in protein-protein interactions. However, the possibility of involving in protein-protein interactions not only the engineered protein fragments containing the motive fusions, but also endogenous proteins should be taken into account.

The use of protein-protein interactions for switching on a cellular process of interest like gene expression has inter alia the following advantages: Firstly, the system may be rendered highly specific, as the function of interest is the result of a highly specific protein-protein or protein-nucleic acid interaction, which is characterized by zero-level uninduced state and absence of non-specific leakiness. This is in contrast to prior art systems such as switches based on small molecules that are inherently less specific and invariably show a certain degree of leakiness. Secondly, a protein-switch or a fragment thereof can be directly delivered into the cells of a plant without a nucleic acid vector encoding said protein or said fragment, thus allowing precise dosage of said protein. This makes direct protein switch delivery into the cell comparable with advantages of using small molecules for triggering a required process in cells. Thirdly, the system is inherently environmentally safer than prior art systems that contain the full genetic information for the protein of interest or the protein switch (either in a form of linear nucleic acid or fragments of said nucleic acid), since it allows that the organism in question does not contain the full genetic information necessary for expression of a functional protein. According to the central dogma of molecular biology, biological systems cannot reverse translate proteins to nucleic acids. Thus, the 'reverse engineering' of the genetic information sufficient for expression of a functional trait by a living organism is impossible. Fourthly, the system provides a specific lock that could be used to prohibit unauthorized use of the system. The use of a protein-switch (notably said second polypeptide) as a component of a crude protein extract from an organism expressing said polypeptide or said protein fragment makes it practically very difficult to identify the active component of said extract.

Spread of the Protein Switch within a Plant for Triggering a Cellular Process of Interest Here, an approach for overcoming the problem of the low number of cells of a plant that can be reached by the externally-applied second polypeptide is provided: said second polypeptide may lead in cells of the plant to the formation of a protein-switch molecule capable of cell-to-cell or systemic movement. Moreover, said second polypeptide may lead to the formation of a virus-based vector (amplicon) expressing a gene of interest or a part thereof and being capable of cell-to cell or systemic movement in said plant. In these approaches, the movement of either viral vectors or protein-switch molecules or both can lead to the spread of a cellular process and/or biochemical cascade over significant parts of said plant and even all over the genetically-modified plant.

In Example 3 of this invention, the protein-switch contains an integrase phC31 to convert a precursor vector of a viral vector into the viral vector. The integrase is split into two inactive fragments that form functional proteins due to intein-mediated trans-splicing of two fragments of the integrase. One of said fragments is delivered into the plant cell as a protein fusion with the virE2 fragment (pICH15085-INT, FIG. 12) with the help of an agrobacterial protein translocation system, while another (pICH15099, FIG. 12) is encoded by plant cell. The viral vector is capable of amplification, cell-to-cell and systemic movement. Integrase-mediated recombination between attP and attB sites of pICHGFPinv (FIG. 7-A) or pICH10921 (FIG. 13) leads to the inversion of a DNA fragment flanked by said recombination sites and formation of a viral vector capable of amplification and expression of the gene of interest (GFP) (FIG. 7-B). This is achieved as the result of placing viral components (3'NTR—3'non-translated region; CP—coat protein) necessary for vector amplification and systemic transport in sense orientation relative to a promoter active in the plant in question like the actin 2 promoter in this example. Thus, together with other viral vector components (RdRp and CP) it forms a cDNA which upon actin 2 promoter-driven transcription forms an RNA viral vector capable of amplification, cell-to-cell and systemic movement. Optionally, said vector can be further modified by removing the CP (coat protein) gene. Such a vector lacking the CP gene will still be capable of cell-to-cell movement.

The construction of plant virus-based expression systems for the expression of non-viral genes in plants has been described in several papers (Dawson et al., 1989, *Virology*, 172, 285-293; Brisson et al., 1986, *Methods in Enzymology*, 118, 659; MacFarlane & Popovich, 2000, *Virology*, 267, 29-35; Gopinath et al., 2000, *Virology*, 267, 159-173; Voinnet et al., 1999, *Proc. Natl. Acad. Sci. USA*, 96, 14147-14152) and reviews (Porta & Lomonossoff, 1996, *Mol. Biotechnol.*, 5, 209-221; Yusibov et al., 1999, *Curr. Top. Microbiol. Immunol*, 240, 81-94) and can be easily performed by those skilled in the art. Viral vector-based expression systems offer a significantly higher yield of a transgene product compared to plant nuclear transgenes. For example, the level of transgenically encoded protein can reach 5-10% of the total cellular plant protein content when expressed from a viral vector (Kumagai et al., 2000, *Gene*, 245, 169-174; Shivprasad et al., 1999, *Virology*, 255, 312-323). RNA viruses are the most suitable as they offer a higher expression level compared to DNA viruses. There are several published patents which describe viral vectors suitable for systemic expression of transgenic material in plants (U.S. Pat. No. 5,316,931; U.S. Pat. No. 5,589,367; U.S. Pat. No. 5,866,785). In general, these vectors can express a foreign gene as a translational fusion with a viral protein (U.S. Pat. No. 5,491,076; U.S. Pat. No. 5,977,438), from an additional subgenomic promoter (U.S. Pat. No. 5,466,788; U.S. Pat. No. 5,670,353; U.S. Pat. No. 5,866,785), or from polycistronic viral RNA using IRES (internal ribosome entry site) elements for independent protein translation (German Patent Application DE 10049587). The first approach—translational fusion of a recombinant protein with a viral structural protein (Hamamoto et al., 1993, *BioTechnology*, 11, 930-932; Gopinath et al., 2000, *Virology*, 267, 159-173; JP6169789; U.S. Pat. No. 5,977,438) gives significant yield of a recombinant protein product. However, the usefulness of this approach is limited, as the recombinant protein cannot be easily separated from the viral one. An alternative of this approach employs a translational fusion via a peptide sequence recognized by a viral site-specific protease or via a catalytic peptide (Dolja et al., 1992, *Proc. Natl. Acad. Sci. USA*, 89, 10208-10212; Gopinath et al., 2000, *Virology*, 267, 159-173; U.S. Pat. No. 5,162,601; U.S. Pat. No. 5,766,885; U.S. Pat. No. 5,491,076). Expression processes utilizing viral vectors built on heterologous subgenomic promoters provide the highest level of protein production to date (U.S. Pat. No. 5,316,931). The most serious disadvantage of viral vectors and many others is their limited capacity with regard to the size of DNA to be amplified. Usually, stable constructs accommodate inserts of not more than one kb. In some areas of plant functional genomics this may not be such a serious limitation, as G. della-Cioppa et al. (WO993651) described the use of TMV-based viral vectors to express plant cDNA libraries with the purpose of silencing endogenous genes. Two-component amplification systems which make use of helper viruses may offer a slightly better capacity (U.S. Pat. No. 5,889,191). Other systems based on expression cassettes that are stably integrated into the plant genome contain the strong 35S promoter driving the expression of viral vector based amplicons. These systems usually are subject to post-transcriptional gene silencing (PTGS) (Angell & Baulcombe, 1997, *EMBO J.*, 16, 3675-3684). The use of PTGS suppressors is necessary to overcome such silencing (WO0138512). It requires to perform crosses between plants carrying the silenced amplicon and plants carrying the source of PTGS suppressor (Mallory et al., 2002, *Nature Biotechnol.*, 20, 622-625) for achieving large scale production of a protein of interest with the help of such system. Evidently, such a system has no flexible and tight control over transgene expression and is restricted to the production of proteins which do not compromise plant growth and development.

Our approach allows to overcome the limitations of the above-described viral vector systems, specifically their limited capacity for the size of the gene to be expressed and the lack of flexibility in controlling the expression. In our invention, the viral vector precursor (or provector) is preferably present in each cell of the transgenic plant. In the case of expression of large genes (above 1 Kb), protein-switch movement is preferred over viral vector movement. Viral vectors can efficiently amplify in cells and the size of the insert of a viral vector mostly affects the ability for cell-to-cell and systemic movement. Therefore, providing a moveable protein-switch capable of activating a viral vector to many cells or even to all cells of the host plant will solve the above-mentioned problem. Additionally, to provide a system with an efficient switching function that is able to turn on the amplification of such a viral vector in most if not all cells of the host plant, protein-switches capable of cell-to-cell/systemic movement are used in the present invention.

To this end, the protein-switch may contain a protein portion that renders said protein capable of cell-to-cell and/or systemic movement. Examples of such protein portions capable of intercellular trafficking are known in prior art. There is evidence that plant transcription factors, defense-related proteins and viral proteins can traffic through plasmodesmata (for review see: Jackson & Hake, 1997, *Curr. Opin. Genet Dev.*, 7, 495-500; Ding, B. 1998, *Plant Mol. Biol.*, 38, 279-310; Jorgensen R A., 2000, *Sci STKE*, 58, PE2; Golz & Hudson, 2002, *Plant Cell*, 14, S277-S288). It was shown that a fusion of 3a movement protein of Cucumber mosaic virus with GFP can traffic out via plasmodesmata to neighboring cells (Itaya et al., 2002, *Plant Cell*, 14, 2071-2083). Such fusion also showed movement through phloem from transgenic rootstock into non-transgenic scion. The movement protein of tobacco mosaic virus (TMV), P30, traffics between cells through plasmodesmata and, by affecting plasmodesmata size, facilitates the movement of many other large macromolecules not specified for such movement (Citovsky et al., 1999, *Phil. Trans. R Soc. London B Biol Sci.*, 354, 637-643; Ding, Itaya & Woo, 1999, *Int Rev. Cytol.*, 190, 251-316). The P30:GFP fusion showed movement between the cells independent of physiological conditions, while the non-targeted GFP diffusion through plasmodesmata at large depends of the physiological state of the plant cells (Crawford & Zambryski, 2001, *Plant Physiol.*, 125, 1802-1812). The fusion of GFP with transcription factor knotted1 also showed the ability for intercellular trafficking. The GFP:KN1 fusion protein demonstrated movement from internal tissues of the leaf to the epidermis, between epidermal cells and into the shoot apical meristem of tobacco plant (Kim et al., 2002, *Proc. Natl. Acad. Sci. USA*, 99, 4103-4108). Plasmodesmata play an important role in such trafficking and its physiological stage and structure are important for the efficiency of such trafficking. For example, simple plasmodesmata allow the nonspecific trafficking of proteins in developing tobacco leaves, while the branched ones do not (Oparka et al., 1999, *Cell*, 98, 5-8). Allowing trafficking of macromolecules including proteins appears to be a normal function of plasmodesmata, which was made use of by plant viruses for their cell-to-cell spread (Fujiwara et al., 1993, *Plant Cell*, 5, 1783-1794). In general, it is evident that plasmodesmata and the phloem play an important role in the transport and delivery of information macromolecules (proteins and nucleic acids) (Ruiz-Medrano et al., 2001, *Curr. Opin. Plant Biol.*, 4, 202-209). Phloem sap proteins from *Cucurbita maxima* and *Ricinum communis* have the capacity of cell-to-cell trafficking through plasmodesmata (Balachandran et al., 1997, *Proc. Natl. Acad. Sci. USA.*, 94, 14150-14155).

FIG. 8 shows schematically possibilities of achieving intercellullar movement of the protein-switch of the invention. An externally-delivered protein switch fragment (i.e. said second polypeptide) and the protein switch synthesized within a cell can be fusions of the same or different protein segments to translocating or trafficking signals. In our example (FIG. 8), the same protein segment, e.g. a recombinase or a fragment thereof is fused either with an intein fragment to mediate trans-splicing, or with a protein portion (TP) providing for intercellular trafficking. It is very likely that for small proteins (like GFP and smaller), fusion to TP might not be necessary, as they may be capable of highly efficient cell-to-cell movement through simple diffusion. However, for larger protein-switches, fusion with a TP or an active fragment thereof is advantageous. It is evident that among all proteins involved in intercellullar trafficking, viral proteins are studied the best. They are the most preferred candidates to be included in a protein-switch. As is shown in FIG. 8, an externally delivered protein switch fragment, after functional complementation by the intracellular protein-switch fragment, triggers the expression of a transgene encoding a protein switch having the same enzymatic activity, but that is capable intercellular trafficking (recombinase:TP). Said protein switch capable of trafficking triggers protein-switch expression in all affected cells, what represents a chain reaction. Availability of said protein switch in the cell is a prerequisite for triggering the expression of a gene of interest (GOI) in cells by DNA rearrangement, causing viral vector-based amlicon formation. The size of the gene of interest expressed from such an amplicon is not a limiting factor for efficient GOI expression, since amplicon stability and cell-to-cell movement are not necessary in this system: the viral provector may be present in each plant cell and the spreading of the protein-switch may trigger the expression of the gene of interest in each of these cells. Preferably, however, spreading of the amplicon contributes to efficient GOI expression.

The ultimate purpose of the protein-switch system contemplated herein is an operational control of a cellular process of interest or a cascade of biochemical reactions of interest in a plant production system. A biochemical cascade is a chain of biochemical reactions in a host production system that ultimately yields a specific product, effect, or trait of interest.

The approaches described herein, in addition to being versatile and leakage-proof, provide an efficient production control method. The two-component process described above is in essence a "key-lock" system, whereby a company can efficiently control access to production by selling the protein-switch component.

Preferred plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing of this invention are including but not restricted to: representatives of Gramineae, Compositeae, Solanaceae and Rosaceae.

Additionally, preferred species for use the invention, as well as those specified above, plants from the genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopo-* dium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea, and the Olyreae, the Pharoideae and many others.

Within the scope of this invention the plant species, which are not included into the food or feed chain are specifically preferred for pharmaceutical and technical proteins production. Among them, Nicotiana species are the most preferred, as the species easy to transform and cultivate with well developed expression vectors (especially viral vectors) systems.

Genes of interest, their fragments (functional or non-functional) and their artificial derivatives that can be expressed as the cellular process of interest and isolated using the present invention include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, E. coli gigA protein, MAPK4 and orthologues, nitrogen assimilation/metabolism enzyme, glutamine synthase, plant osmotin, 2S albumin, thaumafin, site-specific recombinase/integrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabollse lipids, amino acids, sugars, nucleic acids and polysaccharides, superoxide dismutase, inactive proenzyme form of a protease, plant protein toxins, traits altering fiber in fiber producing plants, Coleopteran active toxin from Bacillus thuringiensis (Bt2 toxin, insecticidal crystal protein (ICP), CryIC toxin, delta endotoxin, polyopeptide toxin, protoxin etc.), insect specific toxin AaIT, cellulose degrading enzymes, E1 cellulase from Acidothermus celluloticus, lignin modifying enzymes, cinnamoyl alcohol dehydrogenase, trehalose-6-phosphate synthase, enzymes of cytokinin metabolic pathway, HMG-CoA reductase, E. coli inorganic pyrophosphatase, seed storage protein, Erwinia herbicola lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, Brassica AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, Umbellularia californica C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, D6-desaturase, protein having an enzymatic activity in the peroxysomal b-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, protein having posttranslational cleavage site, DHPS gene conferring sulfonamide resistance, bacterial nitrilase, 2,4-D monooxygenase, acetolactate synthase or acetohydroxyacid synthase (ALS, AHAS), polygalacturonase, Taq polymerase, bacterial nitrilase, many other enzymes of bacterial or phage including restriction endonucleases, methylases, DNA and RNA ligases, DNA and RNA polymerases, reverse trascryptases, nucleases (Dnases and RNAses), phosphatases, transferases etc.

Our invention also can be used for the purpose of molecular farming and purification of commercially valuable and pharmaceutically important proteins including industrial enzymes (cellulases, lipases, proteases, phytases etc.) and fibrous proteins (collagen, spider silk protein, etc.). Any human or animal health protein can be expressed and purified using described in our invention approach. Examples of such proteins of interest include inter alia immune response proteins (monoclonal antibodies, single chain antibodies, T cell receptors etc.), antigens including those derived from pathogenic microorganisms, colony stimulating factors, relaxins, polypeptide hormones including somatotropin (HGH) and proinsulin, cytokines and their receptors, interferons, growth factors and coagulation factors, enzymatically active lysosomal enzyme, fibrinolytic polypeptides, blood clotting factors, trypsinogen, a1-anbtrypsin (AAT), human serum albumin, glucocerebrosidases, native cholera toxin B as well as function-conservative proteins like fusions, mutant versions and synthetic derivatives of the above proteins.

DE 102 54 166 and DE 102 54 165 and the PCT patent applications deriving therefrom contain further examples and disclosure that may be combined with the present invention.

EXAMPLES

Example 1

Intein-Mediated Trans-Splicing of GUS after Agrobacterium-Mediated Transient Expression in Plant Cells The 5' end of the GUS gene was amplified by PCR using primers gusint5 (SEQ ID NO:2) (atg gaa gca gta ctc gac gtc gcc taa aga gag gtt a) and guspr3 (SEQ ID NO:3) (ggc ctg tgg gca ttc agt ctg) from plasmid pICBV33 (35S-omega leader-gus coding sequence-nos terminator in Icon Genetics binary vector pICBV2 (FIG. 9). The 3' end of the GUS gene was amplified by PCR using primers gusint6 (SEQ ID NO:4) (gtc gag tac tgc ttc cat ggc aaa gaa ctg tac agc g) and nosterrev (SEQ ID NO:5) (tca tcg caa gac cgg caa cag g) from plasmid pICBV33 (FIG. 9). These fragments were combined and a second amplification by PCR was made using primers guspr3 and nosterrev. The product of this PCR was digested with BspHI and XbaI and cloned in pICBV33 resulting in plasmid pICH8983 (Annex 2). In this plasmid, the native amino acids 11e370-Pro376 were replaced by the sequence Asp-Val-Glu-Tyr-Cys-Phe-His-Gly (SEQ ID NO:6) derived from the Synechocystis DnaE extein-intein junctions and AatII and NcoI sites were introduced at the beginning and at the end of this modification, respectively.

A DNA fragment containing the N-terminal end of the DnaE intein from *Synechocystis* was amplified by PCR from genomic DNA (Strain PCC6803 from the American Type Culture Center) using primers intNpr1 (SEQ ID NO:7) (gc aagctt gacgtc aag ttt gcg gaa tat tgc ctc agt) and intNpr2 (SEQ ID NO:8) (tcc ctgcag tta ttt aat tgt ccc agc gtc aag). The PCR product was cloned as a HindIII-PstI fragment in pUC19, resulting in plasmid pICH8901. The C-terminal part of the intein was amplified using primers intCpr1 (SEQ ID NO:9) (gg tctaga atcgat g gtt aaa gtt atc ggt cgt cg) and intCpr2 (SEQ ID NO:10) (cg ctgcag ccatgg tt aaa aca att ggc ggc gat cgc) and was cloned as PstI-XbaI fragment in pUC19 (pICH8912, see FIG. 11).

Fusion of the N-intein to the 5'-part of the GUS gene was made by cloning the AatII-XbaI fragment from pICH8901 to pICH8983 (FIG. 10) giving plasmid pICH9303 (FIG. 5). The C-intein was fused to the 3'-part of GUS as ClaI-NcoI fragment, resulting in plasmid pICH9311 (FIG. 5). Both constructs were co-expressed transiently in *Nicotiana benthamiana* leaves using *Agrobacterium*-mediated transient expression (Vaquero et al., 1999, *Proc. Natl. Acad. Sci. USA*, 96, 11128-11133). Gus expression was detected by staining leaves with a solution containing the chromogenic substrate X-gluc (5-bromo-4-chloro-3-indolyl glucuronide) (Jefferson 1987, *Plant Mol Biol Rep*, 5, 387-405). Blue colour indicating GUS activity was visible only when both constructs were co-expressed but not when constructs were expressed individually.

Example 2

Agro-Delivery of the inteinC-GUS3' Fusion Protein

Splitting of the GUS gene and fusion to the *Synechocystis* split DnaE intein was done as described above. An XhoI site preceding the Stop codon of the inteinC-GUS3' fusion was introduced to pICH9723 (Annex 3). The DNA coding for the 37 C-terminal amino acids of the *Agrobacterium tumefaciens* virF protein was synthesized using the two overlapping oligos virFpr3 (SEQ ID NO:11) (gct ctc gag gtt atg gca gaa gtt cgg ccc ata gcc cga tcc att aaa acg gct cac gac gat gcg cga gcg ga) and virFpr4 (SEQ ID NO:12) (cac gga tcc tca tag acc gcg cgt tga tcg agg tct gtc cgc cga cat taa ttc cgc tcg cgc atc gtc gtg ag). The fragment was digested with XhoI-BamHI and ligated in frame to the inteinC-GUS3' fusion, resulting in plasmid pICH10181.

The HindIII (blunted)-XbaI fragment of pICH10181 (FIG. 6) (35S-prom inteinC-GUS3'-virF) was cloned in pICBV12 (FIG. 9) XhoI (blunted)-XbaI, resulting in plasmid pICH10655 (FIG. 6), a small binary vector that doesn't contain any T-DNA sequences. The same was done for the inteinC-GUS3' without virF sequences as negative control (pICH10666, see FIG. 6).

pICH10655 (FIG. 6) and pICH10666 were transformed in *Agrobacterium* strain GV3101 by electroporation. Both constructs were agro-infiltrated into *Nicotiana benthamiana* leaves (Vaquero et al., 1999, *Proc. Natl. Acad. Sci. USA*, 96, 11128-11133) together with pICH9303 (35S-prom GUS5'-inteinN nos-term between T-DNA borders, see FIG. 6). Thus, the GUS5'-inteinN moiety is delivered as DNA and is expressed in the plant cell and the inteinC-GUS3'-virF moiety is delivered as protein. Intein-mediated protein splicing occurs within the plant cell and reconstitutes a functional GUS enzyme. GUS expression was detected by staining leaves with a solution containing the chromogenic substrate X-gluc (5-bromo-4-chloro-3-indolyl glucuronide) (Jefferson 1987, *Plant Mol Biol Rep*, 5, 387-405). Blue colour indicating GUS activity was visible only when both 5'- and 3'-GUS constructs were co-infiltrated but not when constructs were expressed individually or when the negative control construct (pICH10666) was used.

Example 3

Use of Site-Specific DNA Recombination to Assemble Amplifying Vector from Provector Parts Stably Integrated into the Plant Genome: GFP Expression Binary vector pICHFPinv (FIG. 7) carrying T-DNA with two provector parts was designed using standard molecular biology techniques (Maniatis et al., 1982, Molecular cloning: a Laboratory Manual. Cold Spring Harbor Laboratory, New York). The description of provector elements and basic principles of their construction and functioning are described in detail in patent applications PCT/EP02/03476 (WO0288369) and in DE 101 21 283. The vector carries a transformation marker (NPTII gene), the 5'end of TMV preceded by the plant promoter of the *arabidopsis* actn 2 gene (An et al., 1996, Plant J., 10, 107-121) and contains an RNA dependent RNA polymerase (RdRp) and a movement protein (MP) followed by a subgenomic promoter. The vector also contains 3' end of the provector containing a gene of interest (GFP), viral coat protein (CP) providing for the systemic movement and 3'-nontranslated region of the viral vector (3'NTR). The 3' provector together with two transcription termination signals is flanked by recombination sites recognised by phage integrase phiC31 (Thomason, Calendar & Ow, 2001, *Mol. Genet. Genomics*, 265, 1031-1038).

The integrase phiC31 was split in two parts at the position of first cystein and fused to DnaE intein parts. An intein insertion site introducing two Bsa1-sites with different overhangs was cloned into the integrase from an original construct (Thomason, Calendar & Ow, 2001, *Mol. Genet. Genomics*, 265, 1031-1038) by PCR immediately preceding the codon for Cys-405. Corresponding BsaI-sites were also introduced to DnaE intein-N (FIG. 10) and intein-C (FIG. 11)). Intein-N was fused to integrase-N as BsaI-BamHI fragment (pICH15085, FIG. 12) and intein-C was fused to integrase-C as SmaI-BsaI fragment into PstI (blunted with T4 polymerase)-Bsa1 (pICH15099, FIG. 12).

The complete virE-operon from *A. tumefaciens* strain GV3101 (Gene Bank Acc. No. 003065) was amplified by PCR and cloned as XhoI-XbaI fragment into pICBV39 (FIG. 9), a binary vector without border sequences thus preventing DNA transfer (construct pICH15530). Restriction sites for cloning of split integrase were introduced at the same time to the start (NcoI) and close to the end (BsrGI) of virE2. Corresponding restriction sites were also introduced by PCR to both parts of split integrase-intein constructs. Split integrase parts were cloned into this vector leading to a fusion to the 47 C-terminal amino acids of the virE2 protein that are necessary for protein transfer.

The sequence of the T-DNA region of another vector, pICH10921 (FIG. 13), used in the experiments, is shown in ANNEX 1 as SEQ ID No. 1.

Transgenic *Nicotiana benthamiana* and *N. tabacum* plants containing the T-DNA of pICHGFPinv, pICH10921 and pICH15085-INT were obtained by *Agrobacterium*-mediated transformation of leaf discs as described by Horsch et al. (1985, *Science*, 227, 129-131). Leaf discs were incubated for 30 min with *Agrobacterium* strain GV3101 transformed with the construct pICH1754. After three days of incubation on medium (MS-medium 0.1 mg/l NAA, 1 mg/l BAP) without selective agent, selection of transformants was performed on the same MS-medium supplemented with 100 mg/L Kanamycin. In order to reduce the growth of *Agrobacterium*, the medium was also supplemented with 300 mg/L carbenicilin and 300 mg/L cefataxime. Regenerants were incubated on selective MS-medium without hormones supplemented with the same concentration of the selective agents to induce the rooting. The presence of the transgene in segregating T2-populations was confirmed by PCR-analysis.

Exposure of transgenic plant leaves to cell-permeable integrase causes site-specific recombination between attP and attB sites. Such recombination leads to the reversion of 3' provector, thus creating a complete cDNA of a viral amplicon under the control of the actin 2 promoter (FIG. 7, B). The TMV-based RNA amplicon expressing GFP is able for cell-to-cell and systemic movement. The leaves of hybrid progeny between transgenic plants transformed with pICH10921 and pICH15099 were infiltrated with *agrobacteria* carrying the construct pICH15085-INT. GFP expression in *N. benthamiana* plants can be easily detected using a UV lamp or analyzing plant tissue under a LEICA stereo fluorescent microscope system (excitation at 450-490 nm, emission at 500-550 nm). The sGFP used in our experiments can be excited by blue and UV-light.

ANNEX 1: SEQ ID No. 1: The DNA sequence of the T-DNA region of vector pICH10921.

```
tgatgggctgcctgtatcgagtggtgattttgtgccgagctgccggtcggggagctgttggctggctggtggcaggatatattgtggt
gtaaacaaattgacgcttagacaacttaataacacattgcggacgttttaatgtactggggtggatgcaggtcgatctagtaacat
agatgacaccgcgcgcgataatttatcctagtttgcgcgctatattttgttttctatcgcgtattaaatgtataattgcgggactctaatca
taaaaacccatctcataaataacgtcatgcattacatgttaattattacatgcttaacgtaattcaacagaaattatatgataatcatcg
aagaccggcaaacgcgtttcgacaaaatttagaacgaacttaattatgatctcaaatacattgatacatatctcatctagatctag
gttatcattatgtaagaaagttttgacgaatatggcacgacaaaatggctagactcgatgtaattggtatctcaactcaacattatact
tataccaaacattagttagacaaaatttaaacaactatttttatgtatgcaagagtcagcatatgtataattgattcagaatcgttttga
cgagttcggatgtagtagtagccattatttaatgtacatactaatcgtgaatagtgaatatgatgaaacattgtatcttattgtataaata
tccataaacacatcatgaaagacactttctttcacggtctgaattaattatgatacaattctaatagaaaacgaattaaattacgttga
attgtatgaaatctaattgaacaagccaaccacgacgacgactaacgttgcctggattgactcggtttaagttaaccactaaaaaa
acggagctgtcatgtaacacgcggatcgagcaggtcacagtcatgaagccatcaaagcaaaagaactaatccaagggctga
gatgattaattagtttaaaaattagttaacacgagggaaaaggctgtcgacagccaggtcacgttatctttacctgtggtcgaaatg
attcgtgtctgtcgattttaattatttttttgaaaggccgaaaataaagttgtaagagataaacccgcctatataaattcatatattttcctc
tccgctttgaagttttagttttattgcaacaacaacaacaaattacaataacaacaaacaaatacaaacaacaacaacatggca
caatttcaacaaacaattgacatgcaaactctccaagccgctgcgggacgcaacagcttggtgaatgatttggcatctcgtcgcgt
ttacgataatgcagtcgaggagctgaatgctcgttccagacgtcccaaggtaagttctgcatttggttatgctccttgcattttaggtgtt
gctacaggtccacttctccaaggcagtgtctacggaacagacactgattgcaacaaacgcatatccggagttcgagatttccttta
ctcatacgcaatccgctgtgcactccttggccggaggccttcggtcacttgagttggagtatctcatgatgcaagttccgttcggttctc
tgacgtacgacatcggcggtaacttttccgcgcacctttcaaagggcgcgattacgttcactgctgcatgcctaatctggatgtacg
tgacattgctcgccatgaaggacacaaggaagctatttacagttatgtgaatcgtttgaaaaggcagcagcgtcctgtgcctgaat
accagagggcagctttcaacaactacgctgagaacccgcacttcgtccattgcgacaaacctttccaacagtgtgaattgacga
cagcgtatggcactgacacctacgctgtagctctccatagcatttatgatatccctgttgaggagttcggttctgcgctactcaggaa
gaatgtgaaaacttgtttcgcggcctttcatttccatgagaatatgcttctagattgtgatacagtcacactcgatgagattggagctac
ttttcagaagtccggtgataatttaagttttttctttcataatgagagcactctcaattacacccacagttttagtaatataattaagtatgt
gtgtaaaacgttcttcctgctagtcaacggtttgtgtatcataaggagttttagttactagagtcaacacttggtactgtaagtttacga
gagtggatacttttactcttttccgtggtgtgtaccataataatgtggattgcgaagagttttacaaggctatggacgatgcgtggcact
acaaaaagacgttagcaatgcttaatgccgagaggaccatcttcaaggataacgctgcgttaaactttggttcccgaaagtgag
agacatggttatcgtccctctctttgacgcttctatcacaactggtaggatgtctaggagagagattatggtgaacaaggatttcgttta
tacggtcctaaatcacataaaaacgatcaagctaaggctttaacttacgcaaatgttctgtcctttgtggagtctattaggtctagagt
gaaataacggtgtcactgccaggtctgaatgggacacagacaaggcaattctaggtccattagcaatgacattttttccttataac
aaagttgggtcatgtgcaggatgaaataatcctgaaaaagttccagaagttcgacagaaccaccaatgagctgatttggacaag
```

ANNEX 1: SEQ ID No. 1: The DNA sequence of the T-DNA region of vector pICH10921.

```
tctctgcgatgccctgatgggggttattccctcggtcaaggagacgcttgtgcgcggtggttttgtgaaagtagcagaacaagcctt
agagataaaggttcccgagctatactgtacctttgccgacagattggtactacagtacaagaaggcggaggagttccaatcgtgt
gatctttccaaacctctagaagagtcagagaagactacaacgcattatccgagctatcagtgcttgagaatctcgactcttttgactt
agaggcgtttaagactttatgtcagcagaagaatgtggacccggatatggcagcaaaggtggtcgtagcaatcatgaagtcaga
attgacgttgcctttcaagaaacctacagaagaggaaatctcggagtcgctaaaaccaggagaggggtcgtgtgcagagcata
aggaagtgttgagcttacaaaatgatgctccgttcccgtgtgtgaaaaatctagttgaaggttccgtgccggcgtatggaatgtgtcc
taagggtggtggtttcgacaaattggatgtggacattgctgatttccatctcaagagtgtagatgcagttaaaaagggaactatgat
gtctgcggtgtacacagggtctatcaaagttcaacaaatgaagaactacatagattacttaagtgcgtcgctggcagctacagtct
caaacctctgcaaggtgcttagagatgttcacggcgttgacccagagtcacaggagaaatctggagtgtgggatgttaggagag
gacgttggttacttaaacctaatgcgaaaagtcacgcgtggggtgtggcagaagacgccaaccacaagttggttattgtgttactc
aactgggatgacggaaagccggtttgtgatgagacatggttcagggtggcggtgtcaagcgattccttgatatattcggatatggg
aaaacttaagacgctccgtcttgcagtccaaatggtgagcaccggagcctaacgccaaagtaattttggtcgatggtgttcccg
gttgtggaaaaacgaaggagattatcgaaaaggtaaacttctctgaagacttgattttagtccctgggaaggaagcttctaagatg
atcatccggagggccaaccaagctggtgtgataagagcggataaggacaatgttagaacggtggattccttcttgatgcatccttc
tagaagggtgtttaagaggttgtttatcgatgaaggactaatgctgcatacaggttgtgtaaatttcctactgctgctatctcaatgtga
cgtcgcatatgtgtatggggacacaaagcaaattccgttcatttgcagagtcgcgaactttccgtatccagcgcatttttgcaaaactc
gtcgctgatgagaaggaggttagaagagttacgctcaggtgcccggctgatgttacgtatttccttaacaagaagtatgacgggg
cggtgatgtgtaccagcgcggtagagagatccgtgaaggcagaagtggtgagaggaaagggtgcattgaacccaataaccttt
accgttggagggtaaaattttgaccttcacacaagctgacaagttcgagttactggagaagggttacaaggatgtgaacactgtg
cacgaggtgcaaggggagacgtacgagaagactgctattgtgcgcttgacatcaactccgttagagatcatatcgagtgcgtca
cctcatgttttggtggcgctgacaagacacacaacgtgttgtaaatattacaccgttgtgttggacccgatggtgaatgtgatttcaga
aatggagaagttgtccaatttccttcttgacatgtatagagttgaagcgggggtccaatagcaattacagatcgatgcagtattcag
ggacagcaacttgtttgttcagacgcccaagtcaggagattggcgagatatgcaattttactatgacgctcttcttcccggaaacag
tactattctcaatgaatttgatgctgttacgatgaatttgagggatatttccttaaacgtcaaagattgcagaatcgacttctccaaatcc
gtgcaacttcctaaagaacaacctattttcctcaagcctaaaataagaactgcggcagaaatgccgagaactgcaggtttgctgg
aaaatttggttgcaatgatcaaaagaaacatgaatgcgccggatttgacagggacaattgacattgaggatactgcatctctggtg
gttgaaaagttttgggattcgtatgttgacaaggaatttagtggaacgaacgaaatgaccatgacaagggaaagttttttctagatgg
ctttcgaaacaagagtcatctacagttggtcagttagcggactttaactttgtggatttgccggcagtagatgagtacaagcatatga
tcaagagtcaaccaaagcaaaagttagacttgagtattcaagacgaatatcctgcattgcagacgatagtctaccattcgaaaaa
gatcaatgcgattttcggtccaatgttttcagaacttacgaggatgttactcgaaaggattgactcttcgaagtttctgttctacaccag
aaagacacctgcacaaatagaggacttcttttctgacctagactcaacccaggcgatggaaattctggaactcgacatttcgaag
tacgataagtcacaaaacgagttccattgtgctgtagagtacaagatctgggaaaagttaggaattgatgagtggctagctgaggt
atggaaacaaggacacagaaaacgaccttgaaagattatacggccggagtcaaaacatgtctttggtatcaaaggaaaagt
ggtgatgtgacaacctttattggtaataccatcatcattgcagcctgtttgagctcaatgatccccatggacaaagtgataaaggca
gcttttgtggagacgatagcctgatttacattccta&aggtttagacttgcctgatattcaggcgggcgcgaacctcatgtggaactt
cgaggccaaactcttcaggaagaagtatggttacttctgtggtcgttatgttattcaccatgatagaggagccattgtgtattacgatc
cgcttaaactaatatctaagttaggttgtaaacatattagagatgttgttcacttagaagagttacgcgagtctttgtgtgatgtagctag
taacttaaataattgtgcgtatttttcacagttagatgaggccgttgccgaggttcataagaccgcggtaggcggttcgtttgcttttgta
```

ANNEX 1: SEQ ID No. 1: The DNA sequence of the T-DNA region of vector pICH10921.

gtataattaagtatttgtcagataagagattgtttagagatttgttctttgtttgataatgtcgatagtctcgtacgaacctaaggtgagtg atttcctcaatctttcgaagaaggaagagatcttgccgaaggctctaacgaggttaaaaaccgtgtctattagtactaaagatattat atctgtcaaggagtcggagactttgtgtgatatagatttgttaatcaatgtgccattagataagtatagatatgtgggtatcctaggagc tgtttttaccggagagtggctagtgccagacttcgttaaaggtggagtgacgataagtgtgatagataagcgtctggtgaactcaaa ggagtgcgtgattggtacgtacagagccgcagccaagagtaagaggttccagttcaaattggttccaaattactttgtgtccaccgt ggacgcaaagaggaagccgtggcaggttcatgttcgtatacaagacttgaagattgaggcgggttggcagccgttagctctgga agtagtttcagttgctatggtcaccaataacgttgtcatgaagggtttgagggaaaaggtcgtcgcaataaatgatccggacgtcg aaggtttcgaaggtgtggttgacgaattcgcgattcggttgcagcatttaaagcggttgacaacttttaaaagaaggaaaaagaa ggttgaagaaaagggtgtagtaagtaagtataagtacagaccggagaagtacgccggtcctgattcgtttaatttgaaagaaga aaacgtcttacaacattacaaacccgaataatcgataactcgagagtagtgccccaactggggtaacctttgagttctctcagttgg gggcgtagatccgtcgatctagtaacatagatgacaccgcgcgcgataatttatcctagtttgcgcgctatattttgttttctatcgcgt attaaatgataattgcgggactctaatcataaaaaccatctcataaataacgtcatgcattacatgttaattattacatgcttaacgt aattcaacagaaattatatgataatcatcgcaagaccggcaacaggattcaatcttaagaaactttattgccaaatgtttgaacgat ctgcttgactctagctgggcccctacccggggttagggaggattcgaacctctcacttttacttattcccactgtaatacacgtcaaac gtgcgttaacaggtgatccaggaaataaggggtttcgatttaaatggaacccaaaacattgcgtaatttggtttacgccaccccctac ggatttacaccgtaagtctatctcttcgattcaagtggagagaaaaacactatgcgctatcgtgcgcaccacgctctaggggccgc tttacttgtacagctcgtccatgccgtgagtgatcccggcggcggtcacgaactccagcaggaccatgtgatcgcgcttctcgttgg ggtctttgctcagggcggactgggtgctcaggtagtggttgtcgggcagcagcacggggccgtcgccgatgggggtgttctgctg gtagtggtcggcgagctgcacgctgccgtcctcgatgttgtggcggatcttgaagttcaccttgatgccgttcttctgcttgtcggccat gatatagacgttgtggctgttgtagttgtactccagcttgtgccccaggatgttgccgtcctccttgaagtcgatgcccttcagctcgat gcggttcaccagggtgtcgccctcgaacttcacctcggcgcgggtcttgtagttgccgtcgtccttgaagaagatggtgcgctcctg gacgtagccttcgggcatggcggacttgaagaagtcgtgctgcttcatgtggtcggggtagcggctgaagcactgcacgccgta gctgaaggtggtcacgagggtgggccagggcacgggcagcttgccggtggtgcagatgaacttcagggtcagcttgccgtagg tggcatcgccctcgccctcgccggacacgctgaacttgtggccgtttacgtcgccgtccagctcgaccaggatgggcaccaccc cggtgaacagctcctcgcccttgctcaccatggtcaaacaaagaacaaatctctaaccaatctcttatctgacaaatatttaattata ctacaaaaagcaaacgaagcttatcgattttttggatgggtgaggtggagtacgcgcccggggagcccaagggcacgccctgg caccccgcaccgcggcttcgagcaattcatggatcagattgtcgtttcccgccttcagtttaaactatcagtgtttgacaggatatatt ggcgggtaaacctaagagaaaagagcgtttattagaataatcggatatttaaaagggcgtgaaaaggtttatccgttcgtccatttg tatgtgc.

---

The invention claimed is:

1. A method of controlling a genetically-modified plant or plant cells, said method comprising the following steps:
    (a) providing a genetically-modified plant or plant cells, said plant or plant cells containing a heterologous nucleic acid encoding a first polypeptide containing or consisting of a first fragment of a protein, said plant or plant cells further containing an additional heterologous nucleic acid that is controlled by an enzymatic activity of said protein; and
    (b) introducing a second polypeptide into cells of said genetically-modified plant or plant cells by *Agrobacterium* expressibly encoding said second polypeptide, said second polypeptide not being encoded in T-DNA of a Ti-plasmid of said *Agrobacterium*, said second polypeptide containing
        (i) a second fragment of said protein and
        (ii) a virE2 or virF peptide sequence enabling the introduction of said second polypeptide into cells of said genetically-modified plant or plant cells,
whereby said first fragment and said second fragment jointly generate, only when jointly present, an enzymatic activity of said protein by intein-based trans-splicing, said enzymatic activity being the activity of a site-specific recombinase or integrase; said enzymatic activity triggering formation of a DNA, an RNA or a protein of interest from said additional heterologous nucleic acid.

2. The method of claim 1, wherein said enzymatic activity controls a cellular process of interest.

3. The method of claim 1, wherein said enzymatic activity causes the formation of an RNA and/or protein expression product from said additional heterologous nucleic acid.

4. The method of claim 1, wherein said enzymatic activity causes the formation of an expressible amplicon from said additional heterologous nucleic acid or from an expression product thereof.

5. The method of claim 1, wherein said enzymatic activity of said protein causes the formation of a DNA or an RNA amplicon from said additional heterologous nucleic acid, whereby said amplicon has one or more of following capabilities: replication, protein expression, cell-to-cell movement, systemic movement, infective particle assembly, infectivity, suppression of plant's gene silencing ability, modification of the plant's physiological condition.

6. The method of claim 1, wherein said additional heterologous nucleic acid is stably integrated in the nuclear or plastid genome of said plant or plant cells.

7. The method of claim 1, wherein said second polypeptide contains one or more transit or signal peptides for transfer of said second polypeptide to cell organelles selected from the following group: nucleus, plastids, mitochondria, Golgi system, vacuole.

8. The method of claim 1, wherein said protein is capable of cell-to-cell movement or systemic movement in said plant or in a part of said plant.

9. The method of claim 8, wherein said protein contains a domain of a viral movement protein, a domain of a viral coat protein, or a domain of a plant or animal transcription factor capable of cell-to-cell or systemic movement.

10. The method of claim 9, wherein said domain capable of cell-to-cell or systemic movement is an artificially designed polypeptide.

11. The method of claim 1, wherein said plant provided in step (a) is a transgenic plant containing said heterologous nucleic acid stably integrated in the nuclear genome of the cells.

12. The method of claim 1, wherein said plant provided in step (a) is a transgenic plant containing said heterologous nucleic acid stably integrated in the plastid genome of the cells.

13. The method of claim 1, wherein cells of said plant provided in step (a) are transiently transformed with said heterologous nucleic acid.

14. A system for controlling a genetically-modified plant or plant cells, comprising (a) a genetically-modified plant or plant cells containing a heterologous nucleic acid encoding a first polypeptide containing or consisting of a first fragment of a protein, said plant or plant cells further containing an additional heterologous nucleic acid that is controlled by an enzymatic activity of said protein; whereby said genetically-modified plant or plant cells and said first fragment of a protein are adapted for generating an enzymatic activity of said protein from said first fragment and a second fragment of said protein, said enzymatic activity being the activity of a site-specific recombinase or integrase; said enzymatic activity triggering formation of a DNA, an RNA or a protein of interest from said additional heterologous nucleic acid, and
  (b) an *Agrobacterium* expressibly encoding a second polypeptide, said second polypeptide not being encoded in T-DNA of a Ti-plasmid of said *Agrobacterium*, said second polypeptide containing
    (i) a second fragment of said protein and
    (ii) a vir E2 or virF peptide sequence enabling the introduction of said second polypeptide into cells of said genetically-modified plant or plant cells,
whereby said genetically-modified plant or plant cells and said second polypeptide are designed such that said first fragment and said second fragment are jointly capable of generating said enzymatic activity of said protein by intein-based trans-splicing.

15. A method of controlling a genetically-modified plant, said method comprising the following steps:
  (a) providing a genetically-modified plant, said plant containing a heterologous nucleic acid encoding a first polypeptide containing or consisting of a first fragment of a protein, said plant further containing an additional heterologous nucleic acid that is controlled by an enzymatic activity of said protein, wherein said heterologous nucleic acid is stably integrated in the nuclear genome of the cells of said genetically-modified plant; and
  (b) introducing a second polypeptide into cells of said genetically-modified plant by *Agrobacterium* expressibly encoding said second polypeptide, said second polypeptide not being encoded in T-DNA of a Ti-plasmid of said *Agrobacterium*, said second polypeptide containing
    (i) a second fragment of said protein and
    (ii) a virE2 or virF peptide sequence enabling the introduction of said second polypeptide into cells of said genetically-modified plant,
whereby said first fragment and said second fragment jointly generate, only when jointly present, an enzymatic activity of said protein by intein-based trans-splicing, said enzymatic activity being the activity of a site-specific recombinase or integrase; said enzymatic activity triggering formation of a DNA, an RNA or a protein of interest from said additional heterologous nucleic acid.

* * * * *